(12) United States Patent
Harada

(10) Patent No.: US 12,073,558 B2
(45) Date of Patent: Aug. 27, 2024

(54) IMAGE PROCESSING APPARATUS, RADIOGRAPHY SYSTEM, IMAGE PROCESSING METHOD, AND IMAGE PROCESSING PROGRAM

(71) Applicant: FUJIFILM Corporation, Tokyo (JP)

(72) Inventor: Daiki Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 645 days.

(21) Appl. No.: 17/105,863

(22) Filed: Nov. 27, 2020

(65) Prior Publication Data

US 2021/0082114 A1 Mar. 18, 2021

Related U.S. Application Data

(63) Continuation of application No. PCT/JP2019/021320, filed on May 29, 2019.

(30) Foreign Application Priority Data

May 29, 2018 (JP) ................................ 2018-102652

(51) Int. Cl.
G06T 7/00 (2017.01)
A61B 6/00 (2024.01)
A61B 6/50 (2024.01)

(52) U.S. Cl.
CPC ............ G06T 7/0012 (2013.01); A61B 6/482 (2013.01); A61B 6/505 (2013.01); A61B 6/5217 (2013.01);
(Continued)

(58) Field of Classification Search
CPC ......... G06T 7/0012; G06T 2207/10081; G06T 2200/24; G06T 2207/30008;
(Continued)

(56) References Cited

U.S. PATENT DOCUMENTS

2009/0278051 A1 11/2009 Ohara
2010/0284515 A1* 11/2010 Agrawal ................ A61B 6/505
378/55

(Continued)

FOREIGN PATENT DOCUMENTS

JP 9-24039 A 1/1997
JP 2002-159484 A 6/2002

(Continued)

OTHER PUBLICATIONS

Machine translation of JP-2011167388-A (Year: 2011).*

(Continued)

*Primary Examiner* — Aaron W Carter
*Assistant Examiner* — Courtney Joan Nelson
(74) *Attorney, Agent, or Firm* — Birch, Stewart, Kolasch & Birch, LLP

(57) ABSTRACT

An image processing apparatus includes an acquisition unit that acquires a radiographic image captured by a radiography apparatus according to an imaging order including a plurality of examination purposes from the radiography apparatus, a processing unit that performs predetermined processing for each corresponding examination purpose on the radiographic image acquired by the acquisition unit, an output unit that outputs each processing result of the processing performed for each examination purpose by the processing unit to the outside, and a control unit that performs one of a first control for outputting the processing result from the output unit at timings that are considered to be the same and a second control for sequentially outputting the processing result from the output unit in response to an end of the processing, according to settings.

14 Claims, 12 Drawing Sheets

(52) U.S. Cl.
CPC ............... *G06T 2207/10116* (2013.01); *G06T 2207/30008* (2013.01)

(58) Field of Classification Search
CPC .................. G06T 2210/41; G06T 11/00; G06T 2207/10116; A61B 6/505; A61B 17/1703; A61B 2034/105; A61B 2017/00115; A61B 6/5205; A61B 6/5217; A61B 17/1626; A61B 2034/258; A61B 2090/376; A61B 2017/568; A61B 6/463; A61B 5/4509; A61B 2010/009; A61B 2018/00565; A61B 6/461; A61B 5/743; A61B 6/482; G16H 50/20; G16H 30/40; G16H 50/30; G16H 50/00; G16H 30/20; G16H 70/60; G16H 15/00; G06V 2201/03
See application file for complete search history.

(56) References Cited

U.S. PATENT DOCUMENTS

| | | | |
|---|---|---|---|
| 2011/0016430 A1* | 1/2011 | Fram | ..................... G06F 3/0482 715/838 |
| 2011/0135185 A1 | 6/2011 | Gkanatsios et al. | |

FOREIGN PATENT DOCUMENTS

| | | | | | |
|---|---|---|---|---|---|
| JP | 2011-167388 | A | | 9/2011 | |
| JP | 2011167388 | A | * | 9/2011 | |
| JP | 2012-196401 | A | | 10/2012 | |
| JP | 2013-229043 | A | | 11/2013 | |
| JP | 2014-167901 | A | | 9/2014 | |
| JP | 2016-137007 | A | | 8/2016 | |
| KR | 20160056194 | A | * | 11/2014 | |
| WO | WO 2006/080485 | A1 | | 8/2006 | |
| WO | WO-2006080485 | A1 | * | 8/2006 | ............. A61B 6/563 |
| WO | WO-2012128031 | A1 | * | 9/2012 | ............. A61B 6/463 |

OTHER PUBLICATIONS

Machine translation of KR20160056194A (Year: 2014).*
Machine translation of WO-2012128031-A1 (Year: 2012).*
Machine translation of WO-2006080485-A1 (Year: 2006).*
International Preliminary Report on Patentability and Written Opinion of the International Searching Authority for International Application No. PCT/JP2019/021320, dated Dec. 10, 2020, with an English translation.
International Search Report for International Application No. PCT/JP2019/021320, dated Jul. 30, 2019, with an English translation.
Japanese Notice of Reasons for Refusal for Japanese Application No. 2020-522252, dated Apr. 20, 2021, with an English translation.
Extended European Search Report for EP 19812630.2, dated Jul. 20, 2021.

* cited by examiner

IMAGE PROCESSING APPARATUS, RADIOGRAPHY SYSTEM, IMAGE PROCESSING METHOD, AND IMAGE PROCESSING PROGRAM

CROSS-REFERENCE TO RELATED APPLICATIONS

This application is a continuation application of International Application No. PCT/JP2019/021320, filed on May 29, 2019, which is incorporated herein by reference in its entirety. Further, this application claims priority from Japanese Patent Application No. 2018-102652, filed on May 29, 2018, the disclosure of which is incorporated by reference herein.

BACKGROUND

Technical Field

The present disclosure relates to an image processing apparatus, a radiography system, an image processing method, and an image processing program.

Related Art

Conventionally, a plurality of examinations having different purposes may be performed on the same subject. For example, in a case of diagnosing osteoporosis in a subject, an examination corresponding to an examination purpose of observing the subject and an examination corresponding to the examination purpose of measuring at least one of a bone density or a bone mineral content may be performed.

Therefore, in Japanese Patent Application Laid-Open (JP-A) No. 2014-167901 and JP-A No. 2013-229043, for example, a technique is described in which each of a plurality of examination apparatuses provided for each examination purpose performs processing according to the corresponding examination purpose on a radiographic image to obtain a processing result.

However, according to the techniques described in JP-A No. 2014-167901 and JP-A No. 2013-229043, timings at which the processing result corresponding to the examination purpose performed in each of the plurality of examination apparatuses are output from each examination apparatus is not considered, so that a diagnosis using the examination result based on the processing result may not be efficiently performed.

SUMMARY

The present disclosure provides an image processing apparatus, a radiography system, an image processing method, and an image processing program that can efficiently perform a diagnosis using an examination result.

The first aspect of the present disclosure is an image processing apparatus, and the image processing apparatus comprises an acquisition unit that acquires a radiographic image captured by a radiography apparatus according to an imaging order including a plurality of examination purposes from the radiography apparatus, a processing unit that performs predetermined processing for each corresponding examination purpose on the radiographic image acquired by the acquisition unit, an output unit that outputs each processing result of the processing performed for each examination purpose by the processing unit to the outside, and a control unit that performs one of a first control for outputting the processing result from the output unit at timings that are considered to be the same and a second control for sequentially outputting the processing result from the output unit in response to an end of the processing, according to settings.

In the second aspect of the present disclosure according to the first aspect, the timings that are considered to be the same may be timings at which an output interval of the processing result of each of the plurality of processing units is equal to or less than a predetermined threshold value.

The third aspect of the present disclosure is an image processing apparatus, and the image processing apparatus comprises an acquisition unit that acquires a radiographic image captured by a radiography apparatus according to an imaging order including a plurality of examination purposes from the radiography apparatus, a processing unit that performs predetermined processing for each corresponding examination purpose on the radiographic image acquired by the acquisition unit, an output unit that outputs each processing result of the processing performed for each examination purpose by the processing unit to the outside, and a control unit that performs one of a first control for outputting the processing result from the output unit on a condition that two or more processing have been ended and a second control for sequentially outputting the processing result from the output unit to the outside on a condition that each processing has been ended, according to settings.

In the fourth aspect of the present disclosure according to any one of the first to third aspects, the processing unit may have a plurality of examination processing units provided for each examination purpose.

In the fifth aspect of the present disclosure according to any one of the first aspect to the third aspect, the plurality of examination purposes may include observation of a subject and measurement of at least one of a bone density or a bone mineral content of the subject, and the processing unit may include a first processing unit that performs first processing of generating a radiographic image for the observation, and a second processing unit that performs second processing of deriving at least one of the bone density or the bone mineral content.

In the sixth aspect of the present disclosure according to the fifth aspect, the acquisition unit may acquire a first radiographic image captured by irradiating the same subject with radiation of a first energy and a second radiographic image captured by irradiating the same subject with radiation of a second energy different from the first energy from the radiography apparatus, the first processing unit may perform the first processing by using the first radiographic image, and the second processing unit may perform the second processing by using the first radiographic image and the second radiographic image.

In the seventh aspect of the present disclosure according to the sixth aspect, a first radiation detector and a second radiation detector in which a plurality of pixels are disposed, each of which includes a conversion element in which a generated electric charge increases with an increase in a dose of irradiated radiation, may be disposed along a direction of irradiation with the radiation, in the radiography apparatus, the first radiographic image may be a radiographic image generated by the first radiation detector, and the second radiographic image may be a radiographic image generated by the second radiation detector.

In the eighth aspect of the present disclosure according to the sixth aspect, a radiation detector in which a plurality of pixels are disposed, each of which includes a conversion element in which a generated electric charge increases with an increase in a dose of irradiated radiation, may be disposed in the radiography apparatus, the first radiographic image may be a radiographic image generated by the radiation detector due to irradiation with the radiation of the first energy, and the second radiographic image may be a radiographic image generated by the radiation detector due to irradiation with the radiation of the second energy different from the first energy.

In the ninth aspect of the present disclosure according to any one of the fifth aspect to the eighth aspect, the first processing unit may add information representing at least one of the bone density or the bone mineral content derived by the second processing unit to the radiographic image for the observation.

In the tenth aspect of the present disclosure according to any one of the fifth aspect to the ninth aspect, the second processing unit may perform processing of further deriving information on a comparison result between at least one of the bone density or the bone mineral content in the past of the same subject and at least one of the derived bone density or bone mineral content.

The eleventh aspect of the present disclosure is a radiography system, and the radiography system comprises a radiography apparatus that captures a radiographic image according to an imaging order including a plurality of examination purposes, and the image processing apparatus according to the above aspect that acquires the radiographic image from the radiography apparatus.

The twelfth aspect of the present disclosure is an image processing method, and the image processing method includes acquiring a radiographic image captured by a radiography apparatus according to an imaging order including a plurality of examination purposes from the radiography apparatus by an acquisition unit, performing predetermined processing for each corresponding examination purpose on the radiographic image acquired by the acquisition unit, outputting each processing result of the processing performed for each examination purpose to the outside, and performing one of a first control for outputting the processing result at timings that are considered to be the same and a second control for sequentially outputting the processing result in response to an end of the processing, according to settings.

The thirteenth aspect of the present disclosure is an image processing method, and the image processing method includes acquiring a radiographic image captured by a radiography apparatus according to an imaging order including a plurality of examination purposes from the radiography apparatus by an acquisition unit, performing predetermined processing for each corresponding examination purpose on the radiographic image acquired by the acquisition unit, outputting each processing result of the processing performed for each examination purpose to the outside, and performing one of a first control for outputting the processing result on a condition that two or more processing have been ended and a second control for sequentially outputting the processing result to the outside on a condition that each processing has been ended, according to settings.

The fourteenth aspect of the present disclosure is an image processing program, and the image processing program causes a computer to function as an acquisition unit that acquires a radiographic image captured by the radiography apparatus according to an imaging order including a plurality of examination purposes from a radiography apparatus, a processing unit that performs predetermined processing for each corresponding examination purpose on the radiographic image acquired by the acquisition unit, an output unit that outputs each processing result of the processing performed for each examination purpose by the processing unit to the outside, and a control unit that performs one of a first control for outputting the processing result from the output unit at timings that are considered to be the same and a second control for sequentially outputting the processing result from the output unit in response to an end of the processing, according to settings.

The fifteenth aspect of the present disclosure is an image processing program, and the image processing program causes a computer to function as an acquisition unit that acquires a radiographic image captured by a radiography apparatus according to an imaging order including a plurality of examination purposes from the radiography apparatus, a processing unit that performs predetermined processing for each corresponding examination purpose on the radiographic image acquired by the acquisition unit, an output unit that outputs each processing result of the processing performed for each examination purpose by the processing unit to the outside, and a control unit that performs one of a first control for outputting the processing result from the output unit on a condition that two or more processing have been ended and a second control for sequentially outputting the processing result from the output unit to the outside on a condition that each processing has been ended, according to settings.

In addition, the sixteenth aspect of the present disclosure is an image processing apparatus having a processor, the processor including acquiring a radiographic image captured by a radiography apparatus according to an imaging order including a plurality of examination purposes from the radiography apparatus, performing predetermined processing for each corresponding examination purpose on the acquired radiographic image, outputting each processing result of the processing performed for each examination purpose to the outside, and performing one of a first control for outputting the processing result at timings that are considered to be the same and a second control for sequentially outputting the processing result in response to an end of the processing, according to settings.

In addition, the seventeenth aspect of the present disclosure is an image processing apparatus having a processor, the processor including acquiring a radiographic image captured by a radiography apparatus according to an imaging order including a plurality of examination purposes from the radiography apparatus, performing predetermined processing for each corresponding examination purpose on the acquired radiographic image, outputting each processing result of the processing performed for each examination purpose to the outside, and performing one of a first control for outputting the processing result on a condition that two or more processing have been ended and a second control for sequentially outputting the processing result to the outside on a condition that each processing has been ended, according to settings.

According to the above aspect, the image processing apparatus, the radiography system, the image processing method, and the image processing program of the present disclosure can efficiently perform diagnosis using the examination result.

DESCRIPTION OF EMBODIMENTS

Hereinafter, an embodiment example for performing the disclosed technology will be described in detail with reference to the drawings.

First Exemplary Embodiment

Figure 1:
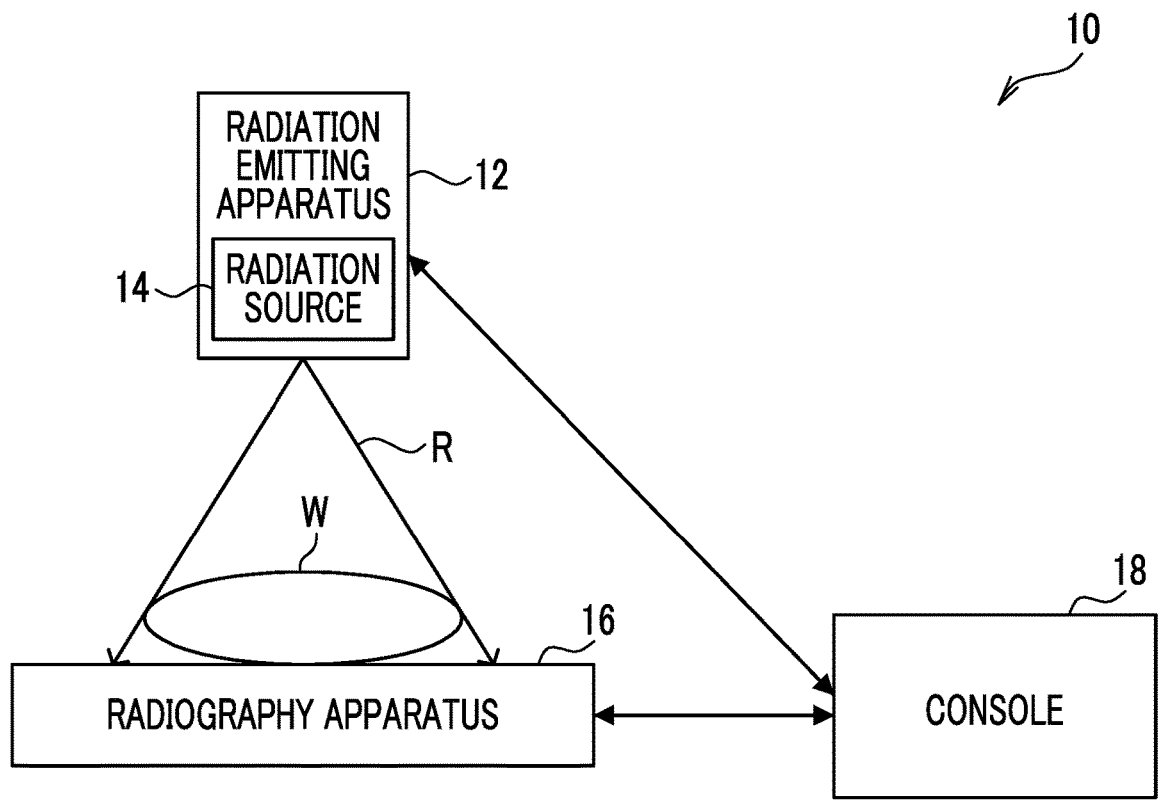
FIG. 1 is a block diagram showing an example of the configuration of a radiography system according to each exemplary embodiment.

First, a configuration of a radiography system 10 according to the present exemplary embodiment will be described with reference to FIG. 1. As shown in FIG. 1, the radiography system 10 comprises a radiation emitting apparatus 12, a radiography apparatus 16, and a console 18. It should be noted that the console 18 is an example of an image processing apparatus according to the present disclosure.

The radiation emitting apparatus 12 according to the present exemplary embodiment comprises a radiation source 14 that irradiates a subject W, which is an example of an imaging target, with radiation R such as X-rays. The radiation emitting apparatus 12 according to the present exemplary embodiment emits the radiation R having a cone-beam shape. An example of the radiation emitting apparatus 12 includes a treatment cart. It should be noted that a method for commanding the radiation emitting apparatus 12 to emit the radiation R is not particularly limited. For example, in a case where the radiation emitting apparatus 12 comprises an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

In a case where the command to emit the radiation R is received, the radiation emitting apparatus 12 emits the radiation R from the radiation source 14 according to set irradiation conditions, such as a tube voltage, a tube current, and an emission period.

Figure 2:
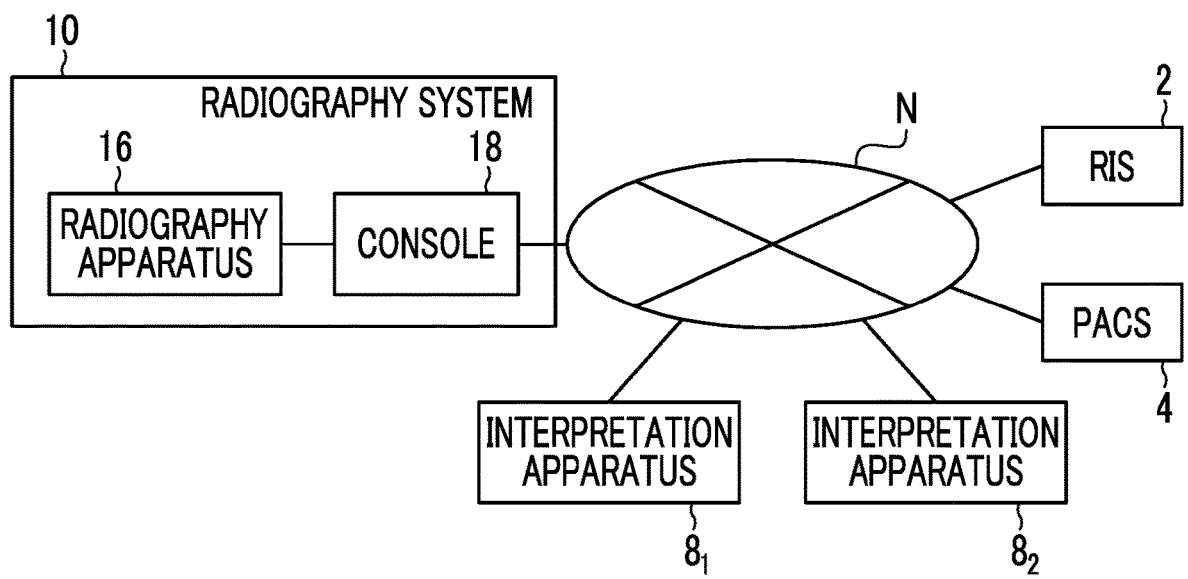
FIG. 2 is a block diagram showing an example of a relationship between a radiography system according to each exemplary embodiment and an external apparatus.

As shown in FIG. 2, as an example, the console 18 of the radiography system 10 according to the present exemplary embodiment is communicatively connected to a radiology information system (RIS) 2 and a picture archiving and communication system (PACS) 4 through a network N.

In the radiography system 10 according to the present exemplary embodiment, the console 18 captures a radiographic image by the radiography apparatus 16 under a control of the console 18 according to an imaging order received from the RIS 2 through the network N or an imaging menu input by a user through the console 18. It should be noted that the "imaging order" is information including subject information of the subject W who captures a radiographic image and information on the radiographic image itself. Specific examples of the subject information include the name, age, sex, height, and weight of the subject W. In addition, the information on the radiographic image capturing includes an examination purpose, a type of imaging such as simple imaging and contrast imaging, an imaging site, an imaging direction, and an imaging condition such as a tube voltage.

In addition, the interpretation apparatus $8_1$ and the interpretation apparatus $8_2$ are communicatively connected to the network N. Each of the interpretation apparatus $8_1$ and the interpretation apparatus $8_2$ is an apparatus used by a doctor or the like who performs diagnosis or the like of the subject W for interpreting the radiographic image captured by the radiography system 10 and interpreting the examination result. A specific example includes so-called viewers and the like. Hereinafter, when each of the interpretation apparatus $8_1$ and the interpretation apparatus $8_2$ is generically referred to without distinction, they are referred to as "interpretation apparatus 8". It should be noted that in the present exemplary embodiment, for convenience of explanation, an aspect in which two interpretation apparatuses 8 (interpretation apparatus $8_1$ and interpretation apparatus $8_2$) are connected to the network N will be described, but the number of interpretation apparatuses 8 connected to the network N is not limited to two.

Figure 3:
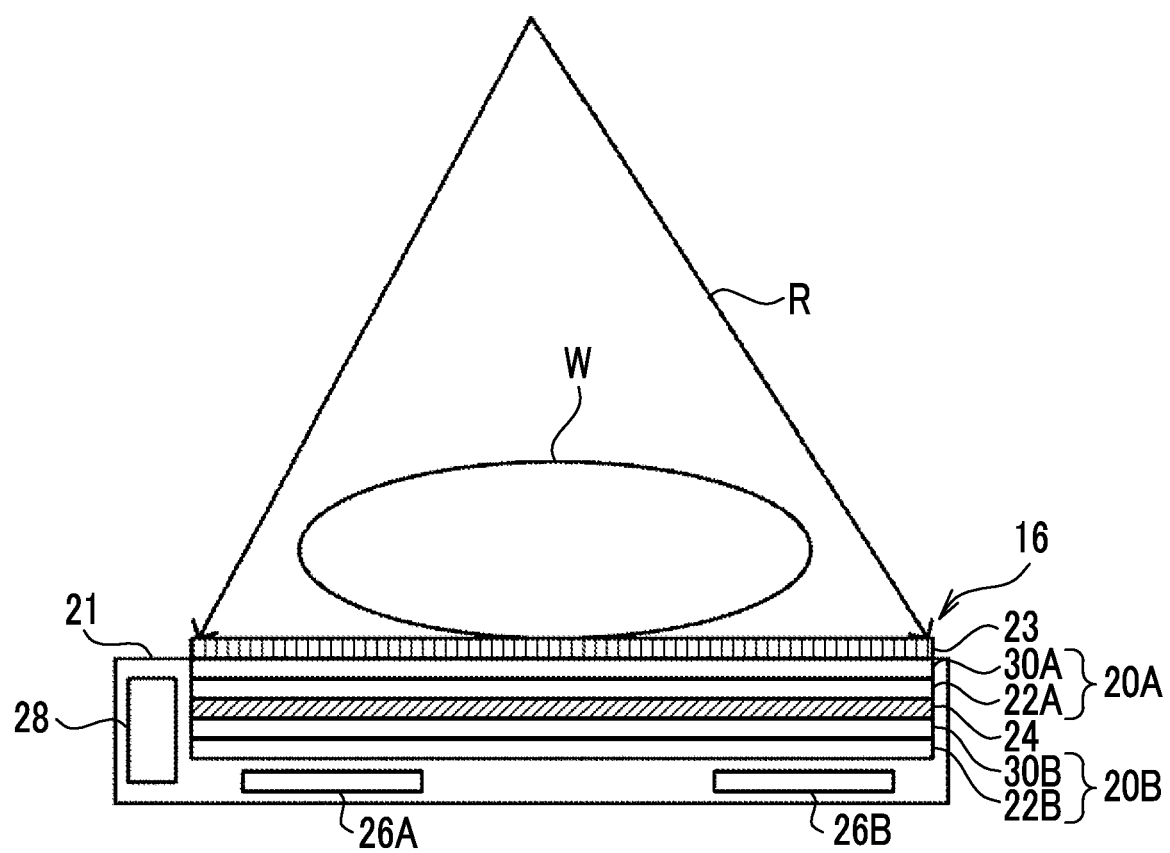
FIG. 3 is a side cross-sectional view showing an example of the configuration of a radiography apparatus according to each exemplary embodiment.

Next, a configuration of the radiography apparatus 16 according to the present exemplary embodiment will be described with reference to FIG. 3. As shown in FIG. 3, the radiography apparatus 16 comprises a plate-shaped housing 21 that transmits the radiation R and has a waterproof, antibacterial, and airtight structure. The housing 21 is provided with the first radiation detector 20A and the second radiation detector 20B that respectively detect the radiation R transmitted through the subject W. In addition, the housing 21 is provided with a radiation limitation member 24, a control substrate 26A, a control substrate 26B, and a case 28. The radiography apparatus 16 captures radiographic images of the subject W by using the first radiation detector 20A and the second radiation detector 20B. Hereinafter, in a case where the first radiation detector 20A and the second radiation detector 20B are generically referred to without distinction, they are generically referred to as "radiation detector 20". It should be noted that a grid 23 for removing scattered rays is disposed between the housing 21 and the subject W.

The first radiation detector 20A is disposed on the incident side of the radiation R and the second radiation detector 20B is disposed so as to be stacked on the side of the first radiation detector 20A from which the radiation R is transmitted and emitted. In addition, the first radiation detector 20A comprises a thin film transistor (TFT) substrate 30A and a scintillator 22A which is an example of a light emitting layer that is irradiated with the radiation R and emits light. Further, the TFT substrate 30A and the scintillator 22A are stacked in the order of the TFT substrate 30A and the scintillator 22A from the incident side of the radiation R. It should be noted that the term "stacked" means a state in which the first radiation detector 20A and the second radiation detector 20B overlap each other in a case where the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction.

In addition, the second radiation detector 20B comprises a TFT substrate 30B and a scintillator 22B which is an example of the light emitting layer. The TFT substrate 30B and the scintillator 22B are stacked in the order of the TFT substrate 30B and the scintillator 22B from the incident side of the radiation R. That is, the first radiation detector 20A and the second radiation detector 20B are irradiation side sampling (ISS) radiation detectors that are irradiated with the radiation R from the side of the TFT substrates 30A and 30B.

In the radiography apparatus 16 according to the present exemplary embodiment, the scintillator 22A of the first radiation detector 20A and the scintillator 22B of the second radiation detector 20B have different compositions. Specifically, for example, the scintillator 22A is configured to include CsI (Tl) (cesium iodide having thallium added thereto) and the scintillator 22B is configured to include gadolinium oxysulfide (GOS). It should be noted that a combination of the composition of the scintillator 22A and the composition of the scintillator 22B is not limited to the above-mentioned example and may be a combination of other compositions or a combination of the same compositions. The scintillators 22A and 22B have different characteristics and the image quality of the generated radiographic image according to the thickness, the diameter of particles, the multi-layered structure of particles, the filling rate of particles, the doping amount of activator, a material, a change in a layer structure, and the presence and absence of a reflecting layer reflecting visible light.

In addition, the grid 23 that removes scattered rays generated by the transmission of the radiation R through the subject W from the radiation R transmitted through the subject W is provided on the side of the first radiation detector 20A on which the radiation R is incident side. For example, the effect of suppressing a reduction in the contrast of a radiographic image is obtained by the removal of the scattered rays from the radiation R and the quality of the radiographic image is improved.

The radiation limitation member 24 that limits the transmission of the radiation R is provided between the first radiation detector 20A and the second radiation detector 20B. An example of the radiation limitation member 24 is a plate-shaped member made of, for example, copper or tin. It should be noted that in a case where the first radiation detector 20A sufficiently absorbs the radiation R, the radiation limitation member 24 may not be provided.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are disposed on the side of the second radiation detector 20B which is opposite to the incident side of the radiation R.

The case 28 is disposed at a position (that is, outside the range of an imaging region) that does not overlap the radiation detector 20 at one end of the housing 21. For example, a power supply unit 69 which will be described below is accommodated in the case 28. It should be noted that the installation position of the case 28 is not particularly limited. For example, the case 28 may be disposed at a position that overlaps the radiation detector 20 on the side of the second radiation detector 20B which is opposite to the incident side of the radiation.

Next, a configuration of a main portion of an electric system of the radiography apparatus 16 according to the exemplary embodiment will be described with reference to FIG. 4.

Figure 4:
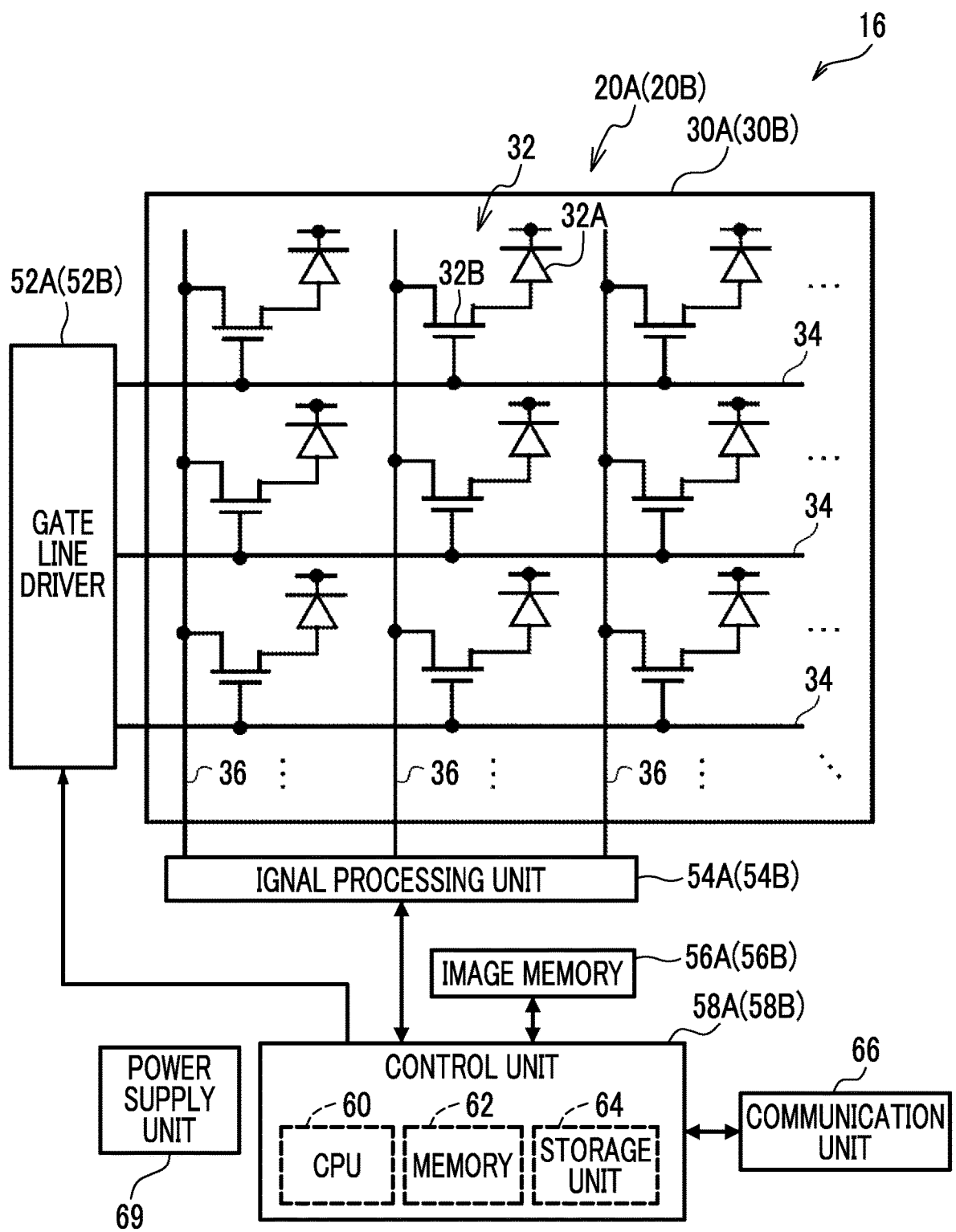
FIG. 4 is a block diagram showing an example of the configuration of a main portion of an electric system of a radiography apparatus according to each exemplary embodiment.

As shown in FIG. 4, a plurality of pixels 32 are two-dimensionally provided in one direction (a row direction in FIG. 4) and a cross direction (a column direction in FIG. 4) that intersects the one direction on the TFT substrate 30A. The pixel 32 is configured with include a sensor unit 32A and a field effect thin film transistor (TFT; hereinafter, simply referred to as a "thin film transistor") 32B.

The sensor unit 32A absorbs the light emitted from the scintillator 22A, generates a charge, and accumulates the generated charge. The thin film transistor 32B converts the charge accumulated in the sensor unit 32A into an electric signal and outputs the electric signal. It should be noted that the sensor unit 32A is an example of the conversion element according to the present disclosure.

A plurality of gate lines 34 which extend in the one direction and are used to turn each thin film transistor 32B on and off are provided on the TFT substrate 30A. In addition, a plurality of data lines 36 which extend in the cross direction and are used to read out the charge through the thin film transistors 32B in an on state are provided on the TFT substrate 30A.

A gate line driver 52A is disposed on one side of two adjacent sides of the TFT substrate 30A and a signal processing unit 54A is disposed on the other side. Each gate line 34 of the TFT substrate 30A is connected to the gate line driver 52A and each data line 36 of the TFT substrate 30A is connected to the signal processing unit 54A.

Each of the thin film transistors 32B of the TFT substrate 30A are sequentially turned on in units of rows by the electric signals which are supplied from the gate line driver 52A through the gate lines 34. The charge which has been read out by the thin film transistor 32B in an on state is transmitted as an electric signal through the data line 36 and is input to the signal processing unit 54A. In this way, the charge is sequentially read out from each row of the thin film transistors and image data indicating a two-dimensional radiographic image is acquired.

The signal processing unit 54A comprises amplifying circuits (not shown) for amplifying an input electric signal and sample-and-hold circuits (not shown) which are provided for each data line 36, and the electric signal transmitted through each of the data lines 36 is amplified by the amplifying circuit and then held in the sample-and-hold circuit. In addition, a multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A comprises a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 69 supplies power to each of the above-mentioned various circuits or elements (for example, the gate line driver 52A, the signal processing unit 54A, the image memory 56A, the control unit 58A, and the communication unit 66). It should be noted that in FIG. 4, lines for connecting the power supply unit 69 to various circuits or elements are not shown in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A and thus the description thereof will not be repeated here. It should be noted that in addition, the control unit 58A and the control unit 58B are connected such that they can communicate with each other.

With the above-mentioned configuration, the radiography apparatus 16 according to the present exemplary embodiment captures radiographic images using the first radiation detector 20A and the second radiation detector 20B. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data". In addition, in a case where the "first radiographic image" and the "second radiographic image" are generically referred to, they are simply referred to as "radiographic images" similarly to the above.

Figure 5:
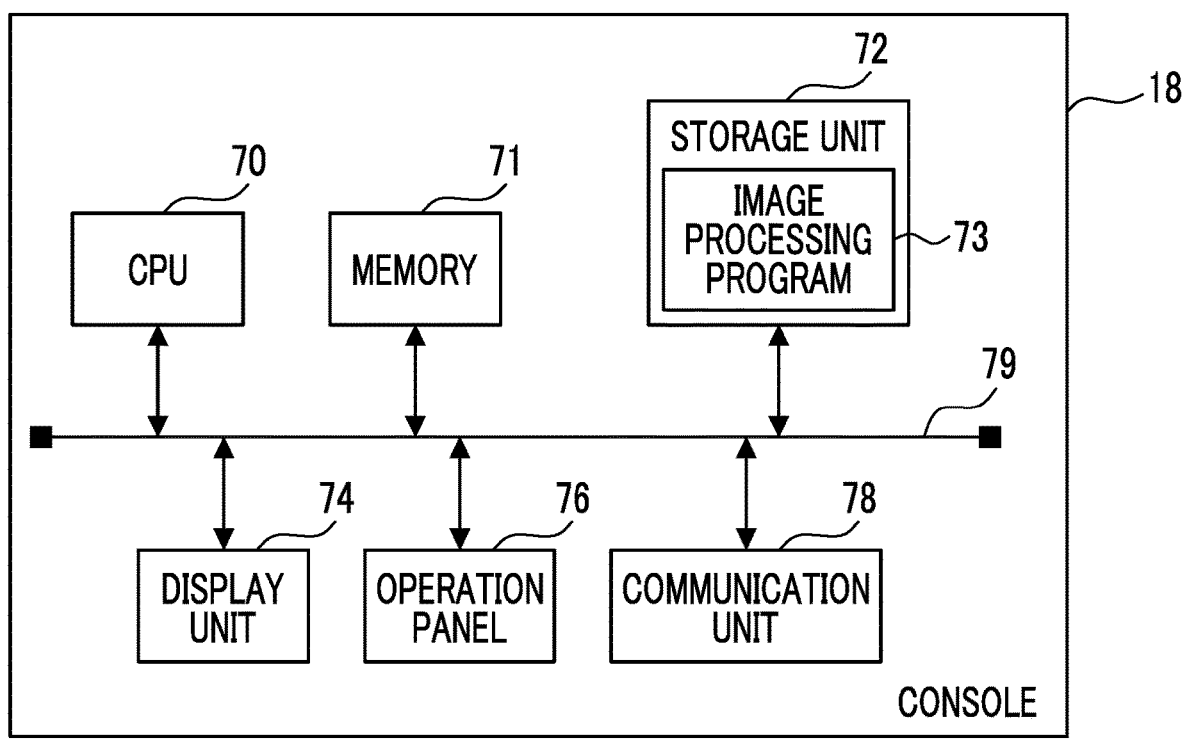
FIG. 5 is a block diagram showing an example of a hardware configuration of a console according to each exemplary embodiment.

Next, with reference to FIG. 5, a hardware configuration of the console 18 according to the present exemplary embodiment will be described. As shown in FIG. 5, the console 18 includes a CPU 70, a memory 71 as a temporary storage region, and a non-volatile storage unit 72. In addition, the console 18 also includes a display unit 74, an operation panel 76, the radiation emitting apparatus 12, the radiography apparatus 16, and a communication unit 78 connected to the network N for communication. The CPU 70, the memory 71, the storage unit 72, the display unit 74, the operation panel 76, and the communication unit 78 are connected to a bus 79.

The storage unit 72 is realized by a hard disk drive (HDD), a solid state drive (SSD), a flash memory, and the like. An image processing program 73 is stored in the storage unit 72 as a storage medium. The CPU 70 reads the image processing program 73 from the storage unit 72, expands the image processing program 73 in the memory 71, and executes the expanded image processing program 73.

The display unit 74 is, for example, a liquid crystal display or the like, and displays an operation menu, a radiographic image obtained by imaging, and the like. In addition, the operation panel 76 is configured to include a plurality of keys and is used in a case where the user inputs various information and operation commands. It should be noted that the display unit 74 and the operation panel 76 may be configured as an integrated touch panel display.

Figure 6:
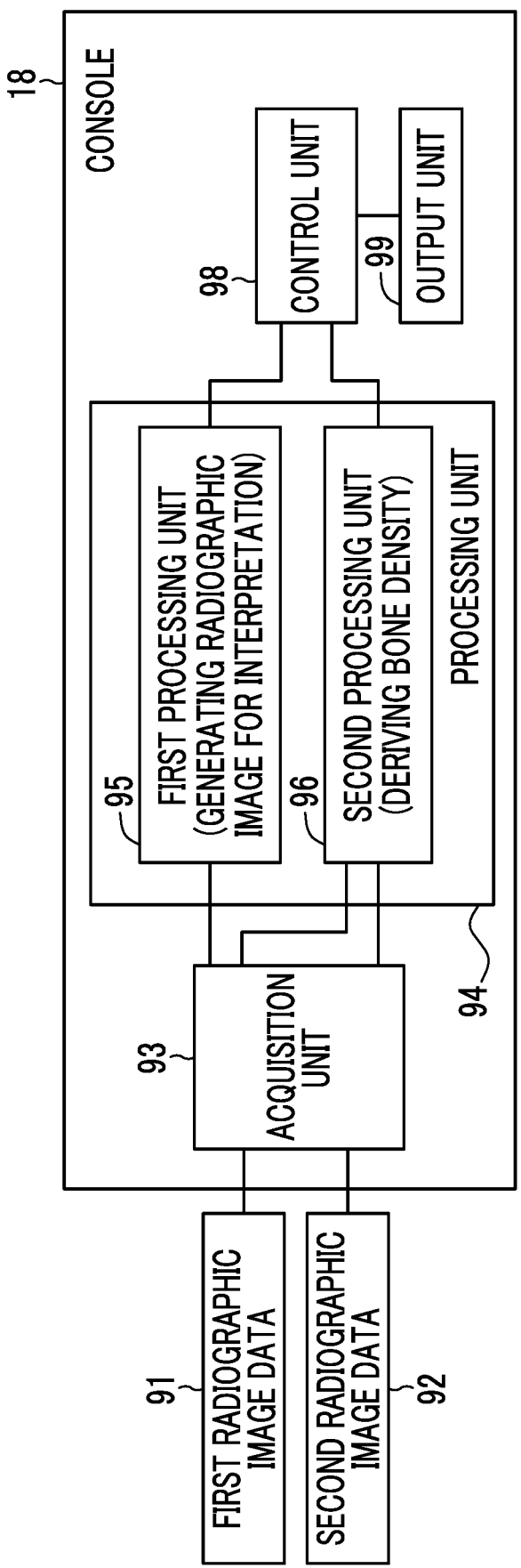
FIG. 6 is a block diagram showing an example of a functional configuration of a console according to each exemplary embodiment.

Next, with reference to FIG. 6, a functional configuration of the console 18 according to the present exemplary embodiment will be described. As shown in FIG. 6, the console 18 has an acquisition unit 93, a processing unit 94, a control unit 98, and an output unit 99. In addition, the processing unit 94 has the first processing unit 95 and a second processing unit 96. By executing the image processing program 73, the CPU 70 functions as the acquisition unit 93, the processing unit 94 (the first processing unit 95 and the second processing unit 96), the control unit 98, and the output unit 99.

The acquisition unit 93 has a function of acquiring the first radiographic image data 91 of the first radiographic image and the second radiographic image data 92 of the second radiographic image from the radiography apparatus 16 through the communication unit 78.

The processing unit 94 has a function of performing predetermined processing for each corresponding examination purpose on the radiographic image acquired by the acquisition unit 93. The first processing unit 95 and the second processing unit 96 according to the present exemplary embodiment are examples of the plurality of examination processing units of the present disclosure.

The first processing unit 95 is a processing unit that performs the first processing corresponding to the first examination for the purpose of observing the subject W and outputs the first processing result. The first processing unit 95 according to the present exemplary embodiment has a function of performing the first processing by using the first radiographic image, and specifically, the first processing unit 95 has a function of generating a so-called radiographic image for an interpretation, which is used for observation of the subject W by a doctor or the like who performs the diagnosis, using the first radiographic image data 91 acquired by the acquisition unit 93, and outputting the radiographic image as the first processing result. The first processing includes, for example, image processing such as offset correction, gain correction, and correction of defective pixels with respect to raw data of the first radiographic image data 91, but is not limited thereto, and preferably includes, for example, image processing corresponding to correction in response to a command from a user or the like.

On the other hand, the second processing unit 96 is the processing unit that performs the second processing corresponding to the second examination for the purpose of measuring the bone density and outputs the second processing result. The second processing unit 96 according to the present exemplary embodiment has a function of performing the second processing by using the first radiographic image and the second radiographic image, and specifically, the second processing unit 96 has a function of deriving the bone density of the subject W using the first radiographic image data 91 and the second radiographic image data 92 acquired by the acquisition unit 93, and outputting information representing the bone density as the second processing result.

Here, an embodiment example of a method of deriving the bone density by the second processing unit 96 according to the present exemplary embodiment will be described.

In the radiography apparatus 16 according to the present exemplary embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of soft-ray components than hard-ray components in energy forming the radiation R, which depends on the material forming the radiation limitation member 24. Therefore, the energy distribution of the radiation R that reaches the second radiation detector 20B has a larger number of hard-ray components than the energy distribution of the radiation R that reaches the first radiation detector 20A.

Since the low-energy components of the radiation R are absorbed first, in the present exemplary embodiment, for example, the energy components of the radiation R that reaches the second radiation detector 20B do not include the low-energy components of the energy components of the radiation R that reaches the first radiation detector 20A. That is, the energy of the radiation R emitted to the first radiation detector 20A is different from the energy of the radiation R emitted to the second radiation detector 20B through the first radiation detector 20A. Therefore, in the radiography apparatus 16 according to the present exemplary embodiment, the radiation detector 20 is irradiated with the radiations R having different energy levels (radiation R with a first energy level and radiation R with a second energy level) and radiographic images are generated by the radiation detector 20.

Thus, the console 18 of the present exemplary embodiment acquires respectively the first radiographic image data 91 generated by the first radiation detector 20A and the second radiographic image data 92 generated by the second radiation detector 20B by irradiating each radiation detector 20 with radiation R of different energy. In addition, the second processing unit 96 of the console 18 derives the ratio of the values of the corresponding pixels of first radiographic image data 91 and second radiographic image data 92 and generates image data for deriving the bone density of the subject W. Hereinafter, the image data for deriving the bone density of the subject W is referred to as a "dual-energy X-ray absorptiometry (DXA) image data" and an image indicated by the DxA image data is referred to as a "DxA image". Specifically, the second processing unit 96 of the console 18 performs log conversion for each pixel value of each of the first radiographic image data 91 and the second radiographic image data 92. Then, the second processing unit 96 generates DxA image data, using an energy subtraction process that subtracts image data obtained by performing log conversion for the second radiographic image data 92 from image data obtained by performing log conversion for the first radiographic image data 91 for each corresponding pixel.

Figure 7:
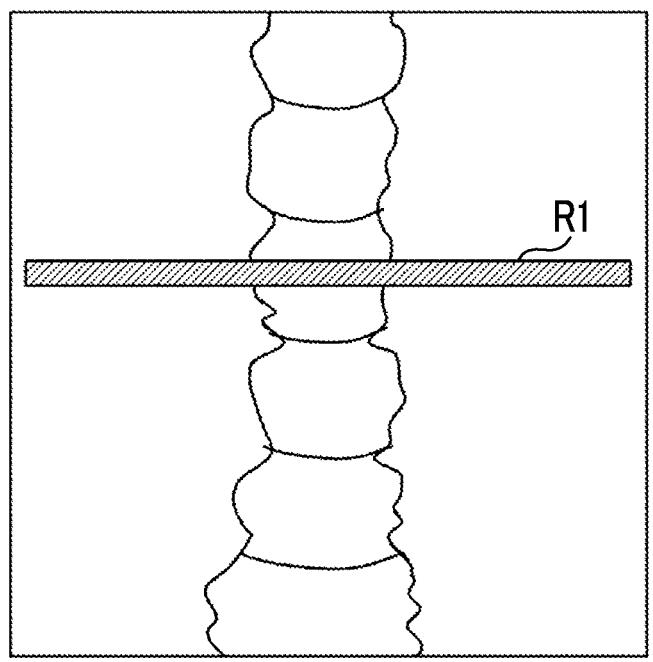
FIG. 7 is a front view showing an example of a region from which a DXA profile used to derive a bone density is to be derived.

In addition, for example, as shown in FIG. 7, the second processing unit 96 according to the present exemplary embodiment derives the bone density from each pixel value (that is, the ratio of the values of the corresponding pixels of the first radiographic image and the second radiographic image and a difference value between the pixel values in a log image) of a bone part of the subject W in the cross-sectional direction (the horizontal direction in the example shown in FIG. 7) in the DxA image.

Figure 8:
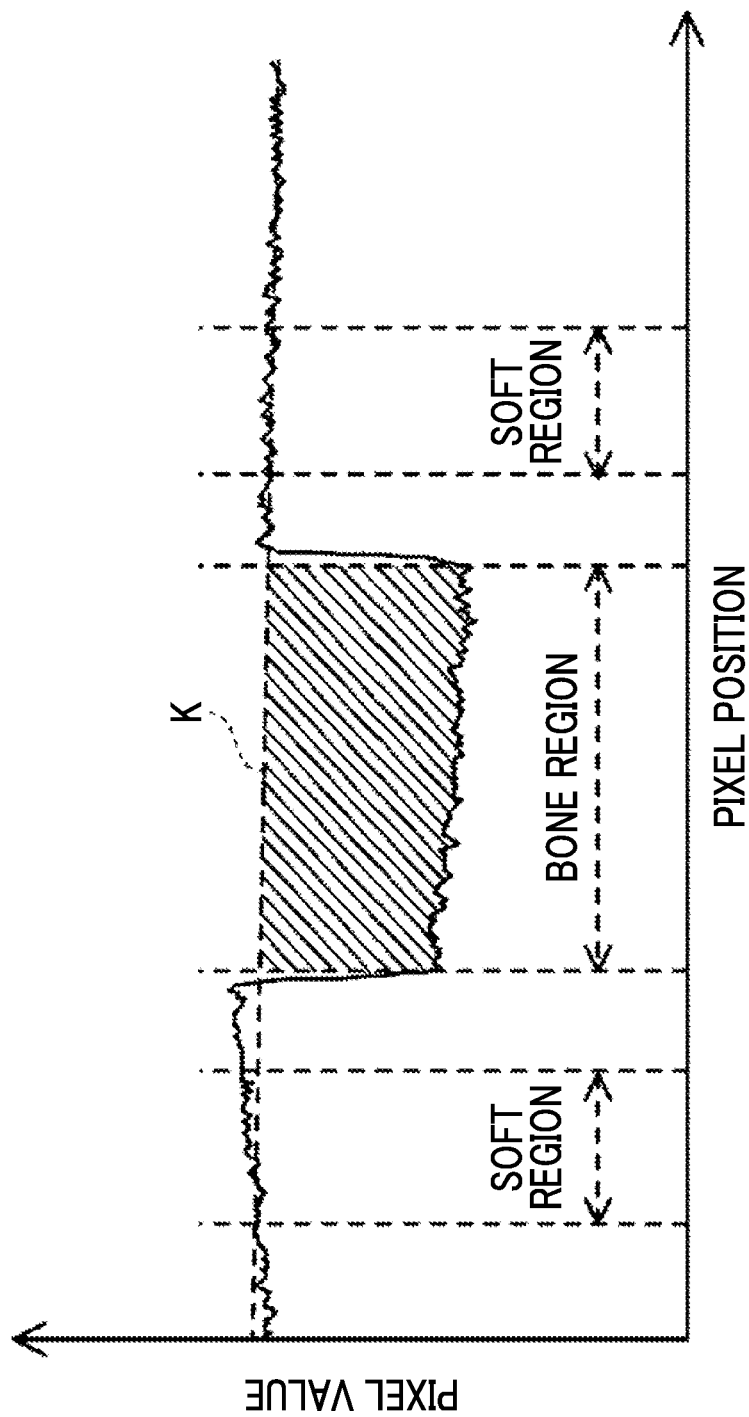
FIG. 8 is a graph showing a bone density derivation processing.

FIG. 8 shows the value of each pixel in a region R1 of the DxA image shown in FIG. 7. It should be noted that the lateral axis in FIG. 8 indicates a pixel position in the horizontal direction of FIG. 7. In addition, the vertical axis in FIG. 8 indicates an average value of the values of a plurality of pixels in the vertical direction of FIG. 7 at each pixel position in the horizontal direction of FIG. 7. Hereinafter, a data group of the pixel values at each pixel position along the horizontal direction of FIG. 7 which is shown in FIG. 8 is referred to as a "DXA profile".

As shown in FIG. 8, for the pixel values in the DXA profile, a pixel value at a pixel position corresponding to a bone tissue of the subject W is less than a pixel value at a pixel position corresponding to a soft tissue. The second processing unit 96 according to the present exemplary embodiment derives the average value of the pixel values in soft tissue regions (hereinafter, referred to as "soft regions") on both sides of a bone tissue region (hereinafter, referred to as a "bone region") and derives a straight line (hereinafter, referred to as a "reference line") K that connects the average values derived at the pixel positions in a central portion of each soft region. In addition, the second processing unit 96 derives the area (area of a hatched portion shown in FIG. 8) of the bone region by integrating a difference between a reference line K and the pixel value for each pixel position of the bone region. The area is a value corresponding to the bone mass of the subject W.

In addition, the second processing unit 96 divides the derived area by the number of pixels corresponding to the width of the bone region to derive the difference between the pixel values of the bone region and the soft region per unit number of pixels. The difference is a value corresponding to the bone density of the subject W. Then, the second processing unit 96 multiplies the derived difference between the pixel values of the bone region and the soft region per unit number of pixels by a predetermined unit conversion coefficient to derive the bone density of the subject W. It should be noted that in the present exemplary embodiment, the pixel position of the region R1 used to derive the DXA profile in the DxA image data, the pixel position of the soft region of the DXA profile, and the pixel position of the bone region are predetermined according to, for example, the subject W and an imaging site.

It should be noted that the method of deriving the bone density by the second processing unit 96 is not limited to the above embodiment. For example, the pixel position corresponding to the bone region and the pixel position corresponding to the soft region may be derived as follows.

The second processing unit 96 subtracts image data obtained by multiplying the first radiographic image data 91 by a predetermined coefficient from image data obtained by multiplying the second radiographic image data 92 by a predetermined coefficient for each corresponding pixel. By performing this subtraction, the second processing unit 96 removes the soft tissue and generates image data (hereinafter referred to as "ES image data") indicating an energy subtraction image (hereinafter referred to as "ES image") indicating an ES image in which the bone tissue is emphasized.

In addition, the second processing unit 96 may specify an edge of a bone region from the ES image in which the bone tissues have been highlighted and may use the specification result as a pixel position corresponding to the bone region in the D×A image data. In this case, for example, the second processing unit 96 estimates the approximate range of the bone region on the basis of the imaging site included in the imaging order. Then, the second processing unit 96 detects pixels that are disposed in the vicinity of the pixels, of which the differential values are equal to or greater than a predetermined value, as the pixels forming the edge (end part) of the bone region in the estimated range to specify the bone region.

In this case, the second processing unit 96 may specify, as the soft region, a region which has a predetermined area including pixels that are separated from the specified edge of the bone region by a distance corresponding to a predetermined number of pixels in a predetermined direction in which the region becomes further away from the bone part. In this case, the second processing unit 96 may use the specification result as a pixel position corresponding to the soft tissue in the D×A image data.

On the other hand, the control unit 98 has a function of performing one of the first control that causes the output unit 99 to output the radiographic image for an interpretation, which is the processing result of the first processing unit 95, and information representing the bone density, which is the processing result of the second processing unit 96, to the outside at timings that are considered to be the same, and a second control that causes the processing result of each of the first processing unit 95 and the second processing unit 96 to be sequentially output (hereinafter referred to as "immediate output") from the output unit 99 to the outside in response to the end of the processing, according to the settings.

Under the control of the control unit 98, the output unit 99 has a function of outputting each of the radiographic images for an interpretation, which is the processing result of the first processing unit 95, and the information representing the bone density, which is the processing result of the second processing unit 96, to the outside.

Figure 9:
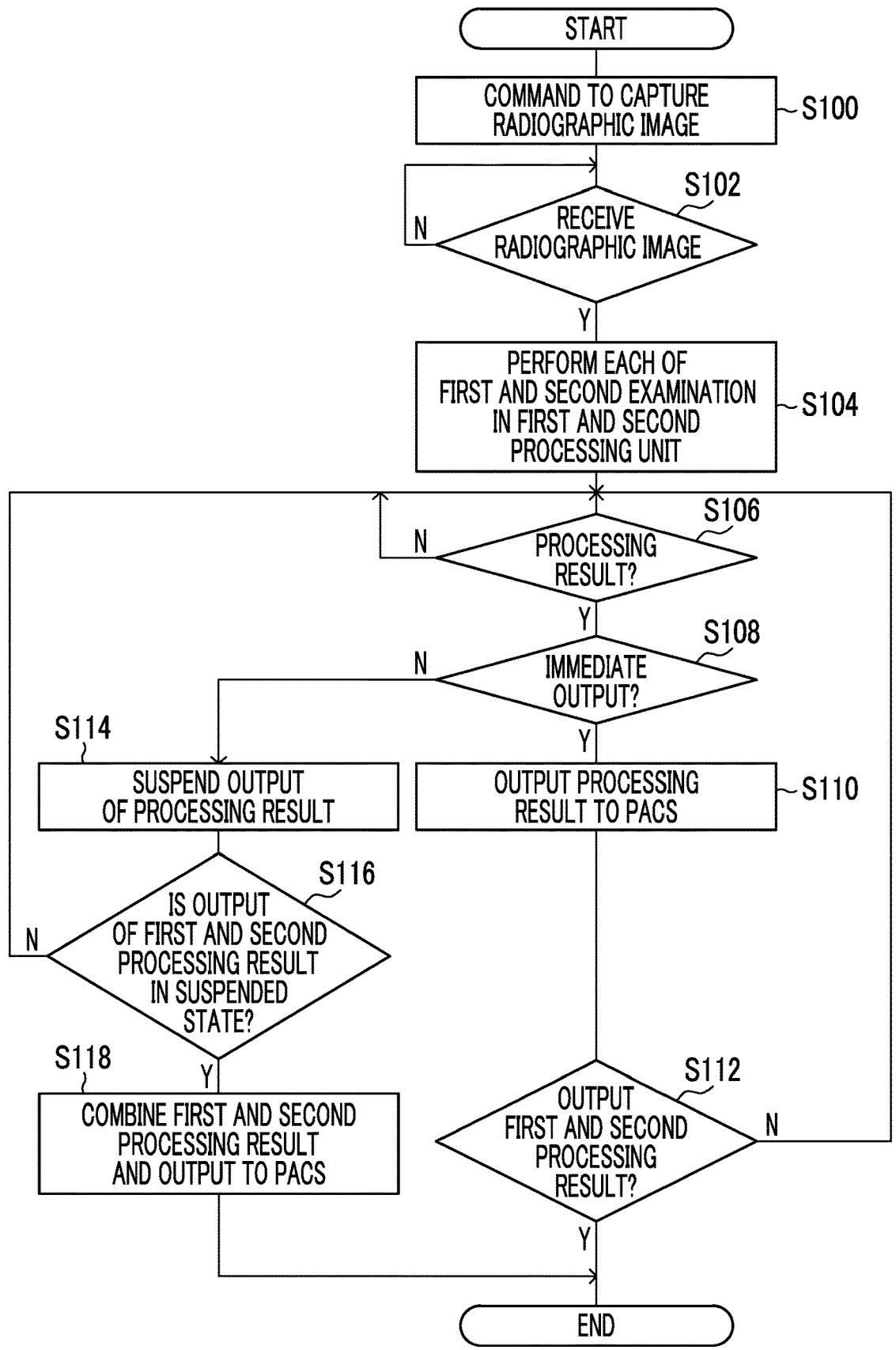
FIG. 9 is a flowchart showing an example of image processing according to the first exemplary embodiment.

Next, the operation of the console 18 of the present exemplary embodiment will be described. FIG. 9 is a flowchart showing an example of a flow of image processing executed by the CPU 70 of the console 18 in a case where the imaging order including the first examination and the second examination as examination purposes is received. The image processing shown in FIG. 9 is performed by the CPU 70 executing the image processing program 73.

In step S100 of FIG. 9, the CPU 70 commands the radiation emitting apparatus 12 and the radiography apparatus 16 to capture a radiographic image. Specifically, the CPU 70 transmits the information included in the received imaging order to the radiography apparatus 16 through the communication unit 78, and transmits the irradiation condition of the radiation R to the radiation emitting apparatus 12 through the communication unit 78. Then, the CPU 70 transmits a command to start the irradiation of the radiation R to the radiography apparatus 16 and the radiation emitting apparatus 12 through the communication unit 78. In a case where the irradiation conditions and the emission start command transmitted from the console 18 are received, the radiation emitting apparatus 12 starts the irradiation of the radiation R according to the received irradiation conditions. The radiation emitting apparatus 12 may comprise an irradiation button. In this case, the radiation emitting apparatus 12 receives the irradiation conditions and the irradiation start command transmitted from the console 18 and starts the irradiation of the radiation R according to the received irradiation conditions in a case where the irradiation button is pressed.

In the radiography apparatus 16, as described above, the first radiographic image is captured by the first radiation detector 20A and the second radiographic image is captured by the second radiation detector 20B according to the radiation R irradiated from the radiation emitting apparatus 12. Then, the first radiographic image data 91 of the first radiographic image and the second radiographic image data 92 of the second radiographic image are output from the radiography apparatus 16 through the communication unit 66.

In the next step S102, the acquisition unit 93 determines whether or not the first radiographic image data 91 and the second radiographic image data 92 have been received through the communication unit 78. The determination in step S102 becomes a negative determination until both the first radiographic image data 91 and the second radiographic image data 92 are received. On the other hand, in a case where both the first radiographic image data 91 and the second radiographic image data 92 are received, the determination in step S102 becomes a positive determination, and the process proceeds to step S104. It should be noted that in the console 18 of the present exemplary embodiment, the received first radiographic image data 91 and second radiographic image data 92 are stored in the storage unit 72.

In step S104, each of the first processing unit 95 and the second processing unit 96 performs the first processing corresponding to the first examination and the second processing corresponding to the second examination. In the present exemplary embodiment, as described above, the first processing unit 95 uses the first radiographic image data 91 to generate a radiographic image for an interpretation, and outputs the image data of the generated radiographic image for an interpretation as the first processing result. In addition, the second processing unit 96 uses the first radiographic image data 91 and the second radiographic image data 92 to derive the bone density, and outputs the information representing the derived bone density as the second examination result.

By the way, the time required for the processing by the first processing unit 95 and the time required for the processing by the second processing unit 96 may be different. In addition, the processing by the first processing unit 95 and the second processing unit 96 may be sequentially performed, and after the processing by one processing unit ends, the processing by the other processing unit may start. In these cases, the timings at which the image data of the radiographic image for an interpretation that is the first processing result is output from the first processing unit 95 is different from the timings at which the information representing the bone density that is the second processing result is output from the second processing unit 96.

Therefore, in the next step S106, the control unit 98 determines whether or not at least one of the first processing result or the second processing result is obtained. In a case where the first processing result by the first processing unit 95 is not obtained and the second processing result by the second processing unit 96 is not obtained, the determination of step S106 becomes a negative determination. On the other hand, in at least one of a case where the first processing result by the first processing unit 95 is obtained or a case where the second processing result by the second processing unit 96 is obtained, the determination in step S106 becomes a positive determination, and the process proceeds to step S108. It should be noted that in a case where both the first processing result and the second processing result are obtained, either one of the processing results is selected, and the processing of each subsequent step is executed.

In the next step S108, the control unit 98 determines whether or not to immediately output the processing result. A method for determining whether or not the control unit 98 performs the immediate output, in other words, whether or not the second control is performed is not particularly limited, and according to the present exemplary embodiment, as an example, the setting in the console 18 or the imaging order is applied. It should be noted that in a case of responding to the setting in the console 18, the setting by the user may be possible by using the operation panel 76 or the like, or the preset contents may be changed by the user by using the operation panel 76 or the like.

In a case where the processing result is immediately output, the determination in step S108 becomes a positive determination, and the process proceeds to step S110. In step S110, the control unit 98 outputs the processing result from the output unit 99 to the PACS 4. It should be noted that the control unit 98 of the present exemplary embodiment associates the first processing result and the second processing result corresponding to the same subject W and one imaging order by assigning the same identifier. Examples of such an identifier include a user identifier (UID) and the like. Therefore, the control unit 98 outputs the processing result (the first processing result or the second processing result) from the output unit 99 to the PACS 4 through the communication unit 78 and the network N after assigning the identifier. It should be noted that in a case where the processing result is immediately output to the PACS 4, the control unit 98 may notify the user by displaying information representing that the processing result is immediately output on the display unit 74. In addition, in this case, it is preferable that the information representing whether only one processing result is immediately output or both processing results are immediately output is also notified.

In the next step S112, the control unit 98 determines whether or not the processing results of both the first processing result and the second processing result have been output from the output unit 99 to the PACS 4. In a case where both processing results are not output to the PACS 4, the determination in step S106 becomes a negative determination and the process returns to step S106. In this case, in a case where the determination in step S106 becomes a positive determination, each processing in steps S108 and S110 is repeated, and then the determination in step S112 becomes a positive determination, and the image processing ends.

On the other hand, in a case where the processing result is not immediately output, in other words, in a case where the first control is performed, the determination in step S108 becomes a negative determination, and the process proceeds to step S114. In step S114, the control unit 98 set the output of the processing result obtained at this point to a suspended state. In a case where the output of the processing result is set to the suspended state, the control unit 98 may notify the user of information representing that the output of the processing result is in the suspended state by displaying the information on the display unit 74 or the like.

In the next step S116, the control unit 98 determines whether or not the output of the processing results of both the first processing result and the second processing result is in the suspended state. In a case where the outputs of both processing results are not in the suspended state, that is, in a case where only the output of one processing result is in the suspended state, the determination in step S116 becomes a negative determination, and the process returns to step S106. In this case, in a case where the determination in step S106 becomes a positive determination, each processing in steps S108, S114, and S116 is repeated, and then the determination in step S115 becomes a positive determination, and the process proceeds to step S118.

In a case where the determination in step S116 becomes a negative determination, the elapsed time after the output of one of the processing results becomes the suspended state is counted, and in a case where the elapsed time exceeds a predetermined time, it is preferable that the user is notified of information representing the fact or information representing a warning or the like.

In step S118, the control unit 98 combines the first processing result and the second processing result, outputs them from the output unit 99 to the PACS 4 at timings that are considered to be the same, and then ends the image processing. In the present exemplary embodiment, as described above, the control unit 98 assigns an identifier, and then outputs each of the first processing result and the second processing result to the PACS 4 from the output unit 99 through the communication unit 78 and the network N at the timings that are considered to be the same. It should be noted that in a case where both the first processing result and the second processing result are output to the PACS 4, the control unit 98 may notify the user of information representing that both processing results are output by displaying the information on the display unit 74.

It should be noted that the "timings that are considered to be the same" of the output of the first processing result and the second processing result only requires that an output interval between the output of the first processing result and the output of the second processing result is equal to or less than a predetermined threshold value, and is not limited to a case where at least a part of the output of one processing result and at least a part of the output of the other processing result are simultaneously performed. In this case, the predetermined threshold value may be determined according to the performance of the CPU 70 or the communication unit 78 of the console 18, the desire of the user, and the like, and is not particularly limited, but it is preferable that the threshold value is sufficiently short to be regarded as simultaneous. As a specific example of the predetermined threshold value, the time from the output of an initial processing result to the output of the next processing result may be within 1 second and within 1 minute.

It should be noted that it is preferable that the first processing result and the second processing result output to the PACS 4 are stored in the storage unit 72 in association with the first radiographic image data 91 and the second radiographic image data 92. The first radiographic image data 91, the second radiographic image data 92, the first processing result, and the second processing result stored in the storage unit 72 may be deleted in order from the oldest one after a predetermined period has elapsed after both the first processing result and the second processing result are output to the PACS 4, or may be deleted according to a command from a user or the like.

As described above, the control unit 98 of the console 18 according to the present exemplary embodiment performs the first control that outputs the first processing result by the first processing unit 95 and the second processing result by the second processing unit 96 to the PACS 4 through the network N at the timings that are considered to be the same, or performs the second control that sequentially outputs the first processing result and the second processing result from the output unit 99 to the PACS 4 according to the end of each of the first processing and the second processing, according to the settings.

Second Exemplary Embodiment

Hereinafter, the second exemplary embodiment will be described in detail. It should be noted that in the present exemplary embodiment, the same components and operations as those described in the first exemplary embodiment are denoted by the same reference numerals, and detailed description thereof is omitted.

The configurations of the radiography system 10, the radiation emitting apparatus 12, and the radiography apparatus 16 of the present exemplary embodiment are the same as each of the first exemplary embodiment, so description thereof will be omitted. On the other hand, in the console 18 of the present exemplary embodiment, some of the functions of the first processing unit 95 are different from the functions of the first processing unit 95 of the first exemplary embodiment, and thus different functions will be described.

The first processing unit 95 of the present exemplary embodiment has a function of adding information representing the bone density, which is the second processing result output by the second processing unit 96, to the radiographic image for an interpretation in addition to the first processing for generating and outputting the radiographic image for an interpretation described above.

Figure 10A:
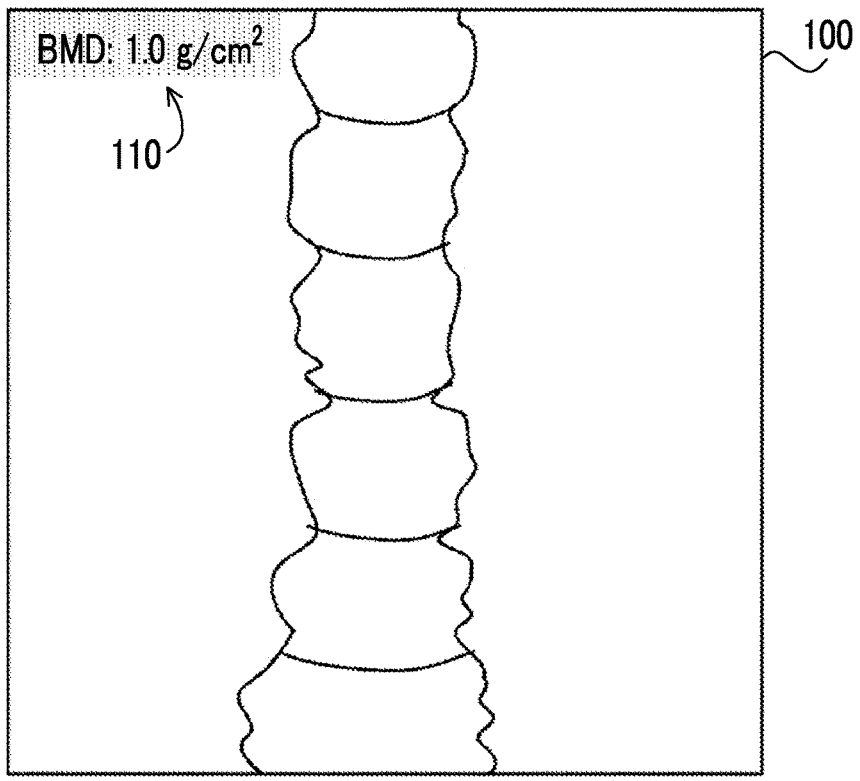
FIG. 10A is an explanatory diagram showing an example of a state in which information representing a bone density is embedded in a radiographic image for an interpretation.
Figure 10B:
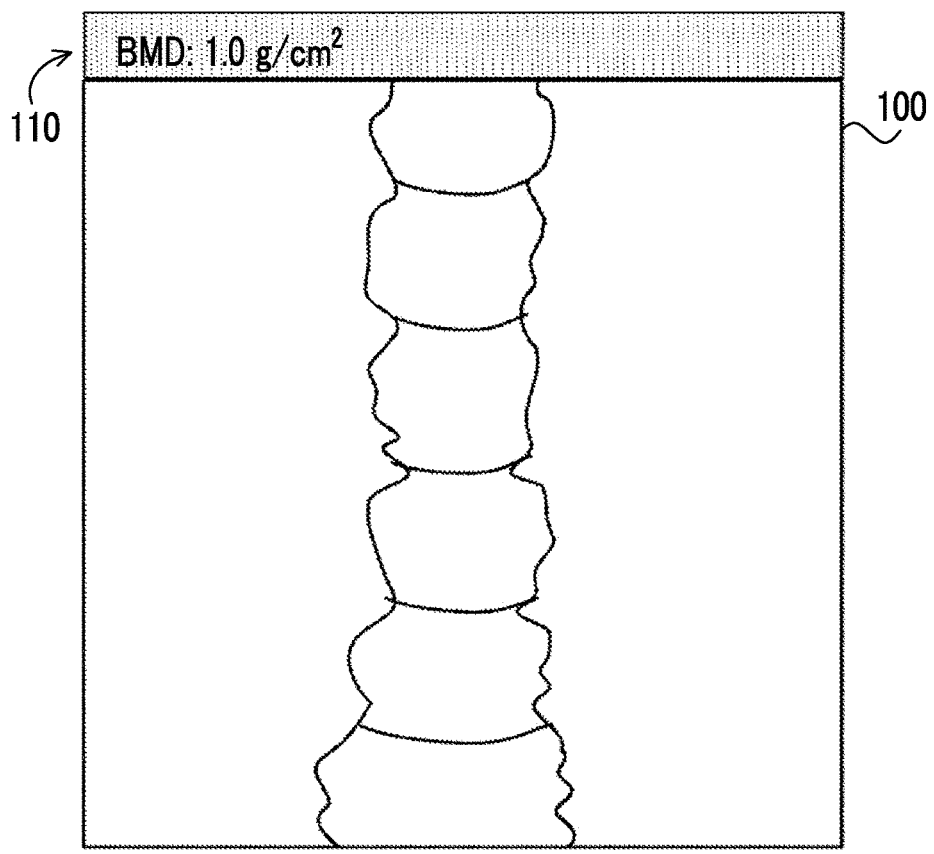
FIG. 10B is an explanatory diagram showing another example of a state in which information representing a bone density is embedded in a radiographic image for an interpretation.

It should be noted that the method by which the first processing unit 95 adds the information representing the bone density to the radiographic image for an interpretation is not particularly limited. For example, as in the example shown in FIG. 10A, image data in which information 110 representing the bone density (bone mineral density (BMD)) is directly embedded in any of the four corners of the radiographic image 100 for an interpretation may be generated. In addition, for example, as in the example shown in FIG. 10B, the image data in which the information 110 representing the bone density is embedded in a header portion of the radiographic image 100 for an interpretation may be generated.

Figure 11A:
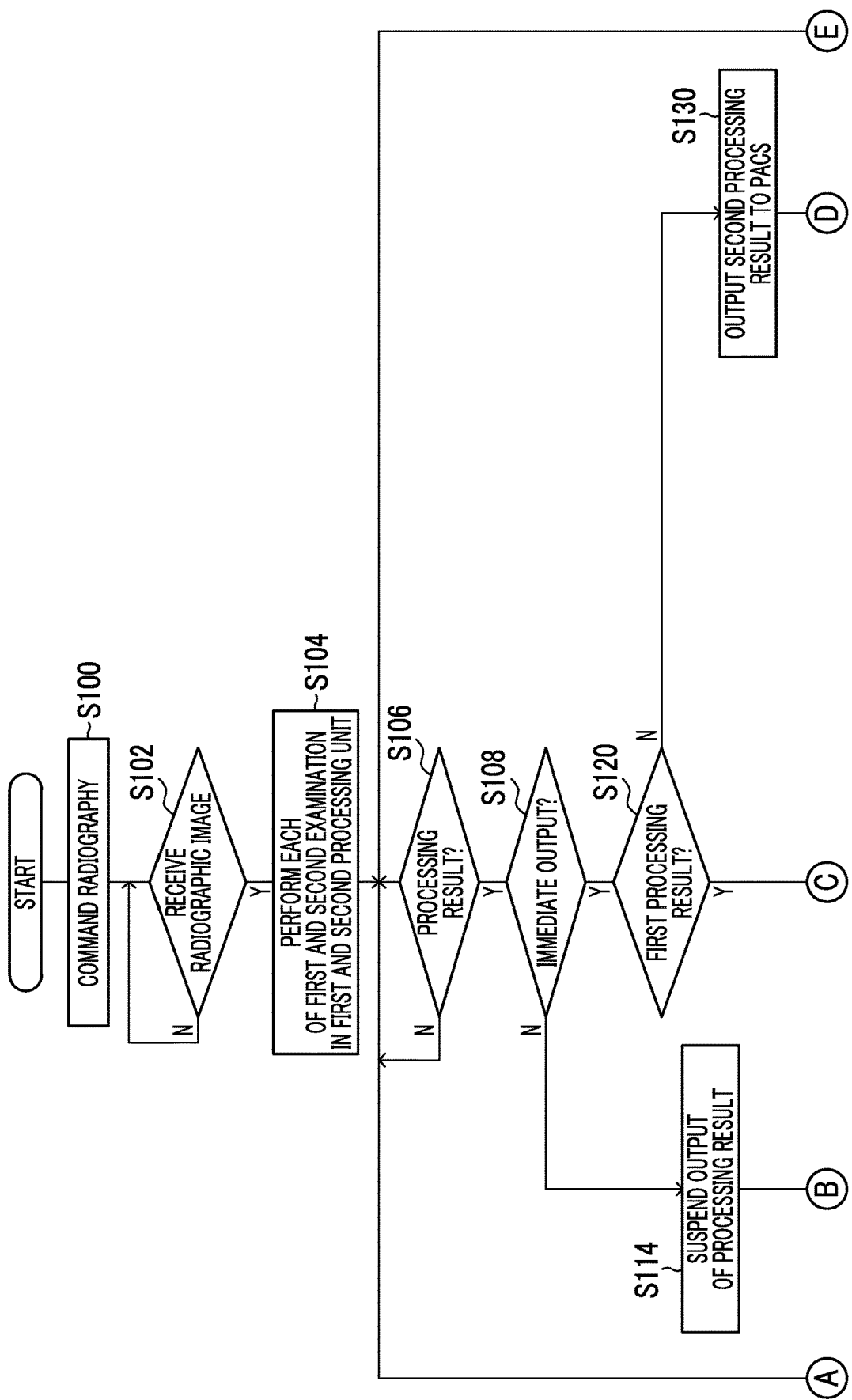
FIGS. 11A and 11B are a flowchart showing an example of image processing according to the second exemplary embodiment.
Figure 11B:
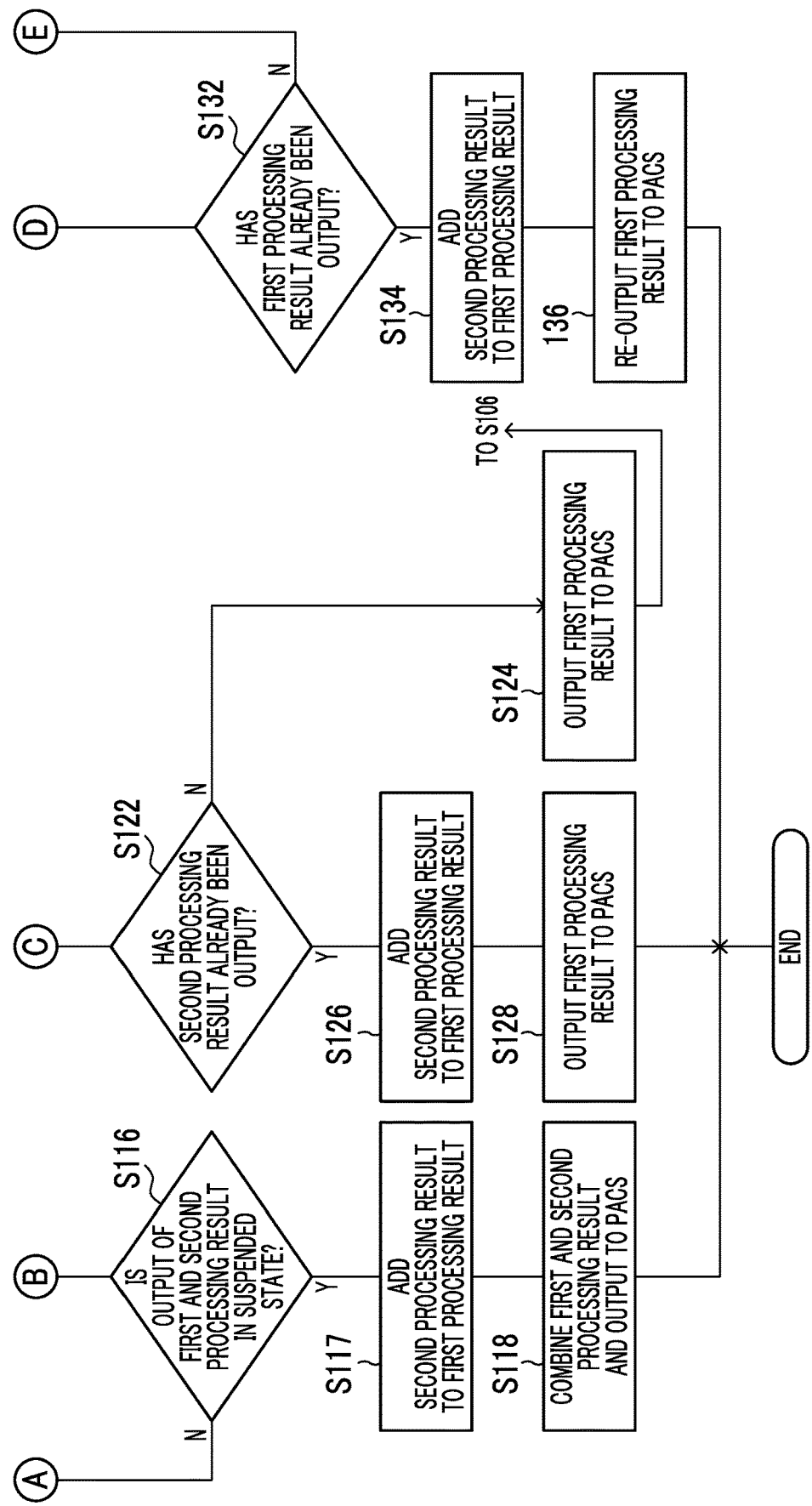

Next, the operation of the console 18 of the present exemplary embodiment will be described. FIGS. 11A and 11B are a flowchart showing an example of the flow of image processing executed by the console 18 of the present exemplary embodiment. As shown in FIGS. 11A and 11B, the image processing according to the present exemplary embodiment is different from the image processing according to the first exemplary embodiment (refer to FIG. 9) in that after a positive determination is made in step S116, the processing in step S117 is executed before the process proceeds to step S118.

In step S117, as described above, the first processing unit 95 performs processing of generating the image data in which the information representing the bone density, which is the second processing result of the second processing unit 96, is added to the radiographic image for an interpretation, which is the first processing result, and sets the generated image data as a new first processing result. In this case, in the next step S118, the same identifiers are assigned to the image data of the radiographic image for an interpretation to which the information representing the bone density is added as the first processing result and the information representing the bone density as the second processing result at the timings that are considered to be the same, and then the same identifiers are output to the PACS 4 through the communication unit 78 and the network N.

In addition, as shown in FIGS. 11A and 11B, the image processing according to the present exemplary embodiment is different from the image processing according to the first exemplary embodiment (refer to FIG. 9) in that, after a negative determination is made in step S116, each processing of steps S120 to S136 is executed instead of steps S110 and S112.

In step S120, the control unit 98 determines whether or not the processing result to be immediately output is the first processing result. In a case where the processing result to be immediately output is the first processing result, the determination in step S120 becomes a positive determination, and the process proceeds to step S122. In step S122, the control unit 98 determines whether or not the second processing result has already been output from the output unit 99 to the PACS 4. In other words, the control unit 98 has already performed processing of step S130, which will be described later, and determines whether or not the second processing result has been output to the PACS 4. In a case where the second processing result has not been output to the PACS 4 yet, the determination in step S122 becomes a negative determination, and the process proceeds to step S124.

In step S124, the control unit 98 outputs the first processing result to which the identifier has been assigned from the output unit 99 to the PACS 4 and then returns to step S106. In this case, the radiographic image for an interpretation, to which the information representing the bone density is not added, is output to the PACS 4.

On the other hand, in a case where the second processing result has already been output to the PACS 4, the determination in step S122 becomes a positive determination, and the process proceeds to step S126. In step S126, similarly to step S117, the first processing unit 95 performs processing of generating the image data in which the information representing the bone density, which is the second processing result of the second processing unit 96, is added to the radiographic image for an interpretation, which is the first processing result, and sets the generated image data as a new first processing result. In the next step S128, the control unit 98 outputs the first processing result to which the identifier has been assigned from the output unit 99 to the PACS 4, and then ends the image processing. In this case, in the processing of step S128, the image data of the radiographic image for an interpretation to which the information representing the bone density is added as the first processing result is output to the PACS 4.

On the other hand, in a case where the processing result to be immediately output is the second processing result, the determination in step S120 becomes a negative determination, and the process proceeds to step S130. In step S130, the control unit 98 outputs the second processing result to which the identifier is assigned, from the output unit 99 to the PACS 4. In the next step S132, the control unit 98 determines whether or not the first processing result has already been output to the PACS 4. In other words, the control unit 98 has already performed the above-described processing of step S124 and determines whether or not the first processing result has been output to the PACS 4. In a case where the first processing result has not been output to the PACS 4 yet, the determination in step S132 becomes a negative determination, and the process returns to step S106.

On the other hand, in a case where the first processing result has already been output to the PACS 4, the determination in step S132 becomes a positive determination, and the process proceeds to step S134. In step S134, similarly to step S126, the first processing unit 95 performs processing of generating the image data in which the information representing the bone density, which is the second processing result of the second processing unit 96, is added to the radiographic image for an interpretation, which is the first processing result, and sets the generated image data as a new first processing result. In the next step S136, the control unit 98 re-outputs the first processing result to which the identifier has been assigned from the output unit 99 to the PACS 4, and then ends the image processing. In this case, in the processing of step S136, the image data of the radiographic image for an interpretation to which the information representing the bone density is added as the first processing result is re-output to the PACS 4. In the PACS 4, the newly received first processing result may be stored instead of the first processing result previously received from the console 18 through the network N, or both of the first processing results may be stored, and it is preferable that either of them can be set by a user or the like.

Therefore, in the console 18 of the present exemplary embodiment, in a case where the first processing by the first processing unit 95 ends before the second processing by the second processing unit 96 in the case of performing the immediate output, the radiographic image for an interpretation is output to the PACS 4 as the first processing result by the processing of step S124. Then, the information representing the bone density is output to the PACS 4 as the second processing result by the processing of step S130. Further, the image data of the radiographic image for an interpretation to which the information representing the bone density is added as the first processing result is re-output to the PACS 4 by the processing of step S136.

On the other hand, in a case where the second processing by the second processing unit 96 ends before the first processing by the first processing unit 95 in the case of performing the immediate output, the information representing the bone density is output to the PACS 4 as the second processing result by the processing of step S130. Next, the image data of the radiographic image for an interpretation to which the information representing the bone density is added as the first processing result is output to the PACS 4 by the processing of step S128.

As described above, the control unit 98 of the console 18 according to the present exemplary embodiment also performs the first control that outputs the first processing result by the first processing unit 95 and the second processing result by the second processing unit 96 to the PACS 4 through the network N at the timings that are considered to be the same, or performs the second control that sequentially outputs the first processing result and the second processing result to the PACS 4 according to the end of each of the first processing result and the second processing result, according to the settings.

As described above, the console 18 according to each exemplary embodiment described above comprises the acquisition unit 93 that acquires, from the radiography apparatus 16, the first radiographic image and the second radiographic image captured by the radiography apparatus 16 according to the imaging order including a plurality of examination purposes, and the processing unit 94 that includes the first processing unit 95 and the second processing unit 96 for performing predetermined processing for each corresponding examination purpose on the first radiographic image and the second radiographic image acquired by the acquisition unit 93. In addition, the console 18 comprises the output unit 99 that outputs each of the first processing result of the first processing unit 95 and the second processing result of the second processing unit 96 performed by the first processing unit 95 and the second processing unit 96 of the processing unit 94 for each examination purpose, to the outside, and the control unit 98 that performs one of the first control for causing the output unit 99 to output the first processing result and the second processing result at the timings that are considered to be the same, and the second control for causing the output unit 99 to sequentially output each of the first processing result and the second processing result in response to the end of the processing, according to the settings.

As described above, the control unit 98 of the console 18 according to each exemplary embodiment described above performs the first control that outputs the first processing result by the first processing unit 95 and the second processing result by the second processing unit 96 to the PACS 4 through the network N at the timings that are considered to be the same, or performs the second control that sequentially outputs the first processing result and the second processing result to the PACS 4 according to the end of each of the first processing result and the second processing result, according to the settings.

Since the first control performed by the control unit 98 of the console 18 outputs the first processing result and the second processing result to the PACS 4 at the timings that are considered to be the same, for example, a doctor who diagnoses osteoporosis or the like can acquire image data of a radiographic image for an interpretation and information representing bone density from the PACS 4 through the network N to the interpretation apparatus 8 used for diagnosis at the timings that are considered to be the same.

For example, in a case where one doctor diagnoses osteoporosis as the interpretation apparatus 8 using the interpretation apparatus 8$_1$ or the interpretation apparatus 8$_2$ for a diagnosis, it may be preferable to perform the diagnosis from an observation result of the subject W by the radiographic image for an interpretation and a value of the bone density. In this case, the image data of the radiographic image for an interpretation and the information representing the bone density can be acquired at the timings that are considered to be the same, and can be used for a diagnosis, so that the diagnosis using the examination result can be efficiently performed. It should be noted that in this case, it is preferable that the radiographic image 100 for an interpretation and the information 110 representing the bone density are displayed at the same time on a display unit (not shown) such as a monitor of the interpretation apparatus 8, or the display of the radiographic image 100 for an interpretation and the display of the information 110 representing the bone density are switched according to a command from a doctor.

In addition, by the second control performed by the control unit 98 of the console 18 and sequentially output to the PACS 4 according to the end of the first processing and the second processing, for example, a doctor who diagnoses osteoporosis or the like can sequentially acquire the image data of the radiographic image for an interpretation and the information representing the bone density from the PACS 4 through the network N to the interpretation apparatus 8 used for a diagnosis.

For example, there are two doctors who diagnose osteoporosis, and there is a case where a doctor who performs the diagnosis from the observation result of the subject W by using the interpretation apparatus 8$_1$ for the diagnosis and a doctor who performs the diagnosis by bone density by using the interpretation apparatus 8$_2$ for a diagnosis are different. In such a case, it is sufficient for both doctors to acquire the processing result required for their own diagnosis from the PACS 4 through the network N to the interpretation apparatus 8 used for their own diagnosis. Therefore, even in a case where both the image data of the radiographic image for an interpretation and the information representing the bone density are not output to the PACS 4, the doctor who performs the diagnosis can start the diagnosis in a case where the processing results (the image data of the radiographic image for an interpretation or the information representing the bone density) required for their own diagnosis can be acquired, so that the diagnosis using the examination results can be performed efficiently.

Therefore, according to the console 18 according to each exemplary embodiment described above, it is possible to efficiently perform the diagnosis using the examination result.

It should be noted that the control unit 98 according to each embodiment described above may have a function of performing one of the first control that outputs from the output unit 99 the radiographic image for an interpretation, which is the processing result of the first processing unit 95, and the information representing the bone density, which is the processing result of the second processing unit 96, on the condition that two or more processing have been ended, and the second control that sequentially outputs from the output unit 99 to the outside on the condition that each processing has been ended, according to the setting.

Also in this aspect, the console 18 performs the first control that outputs a plurality of processing results to the PACS 4 through the network N, or performs the second control that sequentially outputs the plurality of processing results to the PACS 4 according to each of the end of the first processing and the end of the second processing, on the condition that two or more processing are ended according to the setting. Therefore, according to the console 18 according to each exemplary embodiment described above, it is possible to efficiently perform the diagnosis using the examination result.

It should be noted that in each exemplary embodiment described above, an aspect in which the second processing unit 96 derives the bone density as the second processing is described, but the present invention is not limited to each exemplary embodiment described above, and the second processing may be an aspect in which an analysis result obtained by analyzing the value of the bone density in addition to the value of the bone density itself is derived, and a bone density report including the value of the bone density and the analysis result is generated. In this case, as the analysis of the value of the bone density, for example, an average value of the bone density according to the age, sex, and the like, such as a young adult mean (YAM) value of the bone density, may be used, and the average value according to the age, sex, and the like of the subject W may be compared with a value of bone density of the subject W. In this case, information representing how much the bone density of the subject W is compared with the average value, for example, whether or not the bone density is appropriate for the year, is obtained as an analysis result.

For example, as the analysis result of the bone density, the derived value of the bone density may be stored in the storage unit 72 of the console 18 or the PACS 4 in association with information such as an identifier representing the subject W, whereby the value of bone density stored in the past may be compared with the value of the bone density derived this time, for the same subject W. In this case, information representing a change in the bone density such as the bone density decreasing or rising can be obtained as the analysis result. Furthermore, in this case, in a case where the value of the bone density derived this time is lower than a predetermined threshold value than the value of bone density obtained in the past, it is preferable that the analysis result includes information for calling attention and warnings. As a specific example, in a case where the value of the bone density derived this time is reduced by 10% or more from the previous value of the bone density, a simple moving average value of the value of bone density obtained in the past, a weighted moving average value of the value of bone density obtained in the past, and the like, it is preferable that the analysis result includes information for calling attention and warnings. In this case, in a case where the information (age, sex, and the like) of the subject W is changed by a command or the like of a user input through the operation panel 76, it is preferable to re-analyze according to the changed information of the subject W.

In addition, the second processing unit 96 may derive the bone mineral content instead of the bone density or together with the bone density as the second processing.

In each exemplary embodiment described above, an aspect in which the first radiographic image data 91 is used for the first processing of the first processing unit 95 is described, but it is not limited to the aspect, and for example, an aspect in which the first processing is performed by using the first radiographic image data 91 and the second radiographic image data 92 may be adopted.

In the second exemplary embodiment, an aspect in which the second processing result by the second processing unit 96 is added to the first processing result by the first processing unit 95 is described, but the present invention is not limited to the aspect, and for example, the first processing result by the first processing unit 95 may be added to the second processing result by the second processing unit 96. In this case, for example, the second processing unit 96 may perform the second processing of generating a bone density report to which an image obtained by reducing the radiographic image for an interpretation that is the first processing result is attached.

In addition, the examination purpose and the processing content of the first processing unit 95 and the second processing unit 96 described in each exemplary embodiment described above are examples, and it goes without saying that the present invention is not limited to those described in each exemplary embodiment described above. Further, the number of examination purposes included in the imaging order is not limited to each exemplary embodiment described above, and the console 18 may comprise a processing unit for each examination purpose. It should be noted that the number of examination purposes included in the imaging order may be one. In this case, for example, the console 18 may be configured to collectively execute a plurality of imaging orders for the same subject W.

In each exemplary embodiment described above, an aspect in which one radiography apparatus 16 captures a radiographic image (the first and second radiographic images) corresponding to a plurality of examination purposes for an examination purpose of observing the subject W and an examination purpose of measuring bone density is described, but the radiography apparatus 16 is not limited to the aspect. For example, a radiographic image may be captured by different radiography apparatuses for each examination purpose.

In each exemplary embodiment described above, the image processing (refer to FIGS. 9, 11A and 11B) executed by the console 18 may be executed by the control unit 58A or the control unit 58B of the radiography apparatus 16. In addition, in the case where the radiography apparatus 16 has a configuration having an overall control unit that controls the overall operation of the control unit 58A and the control unit 58B, the supervising control unit may execute image processing (refer to FIGS. 9, 11A and 11B).

Figure 12:
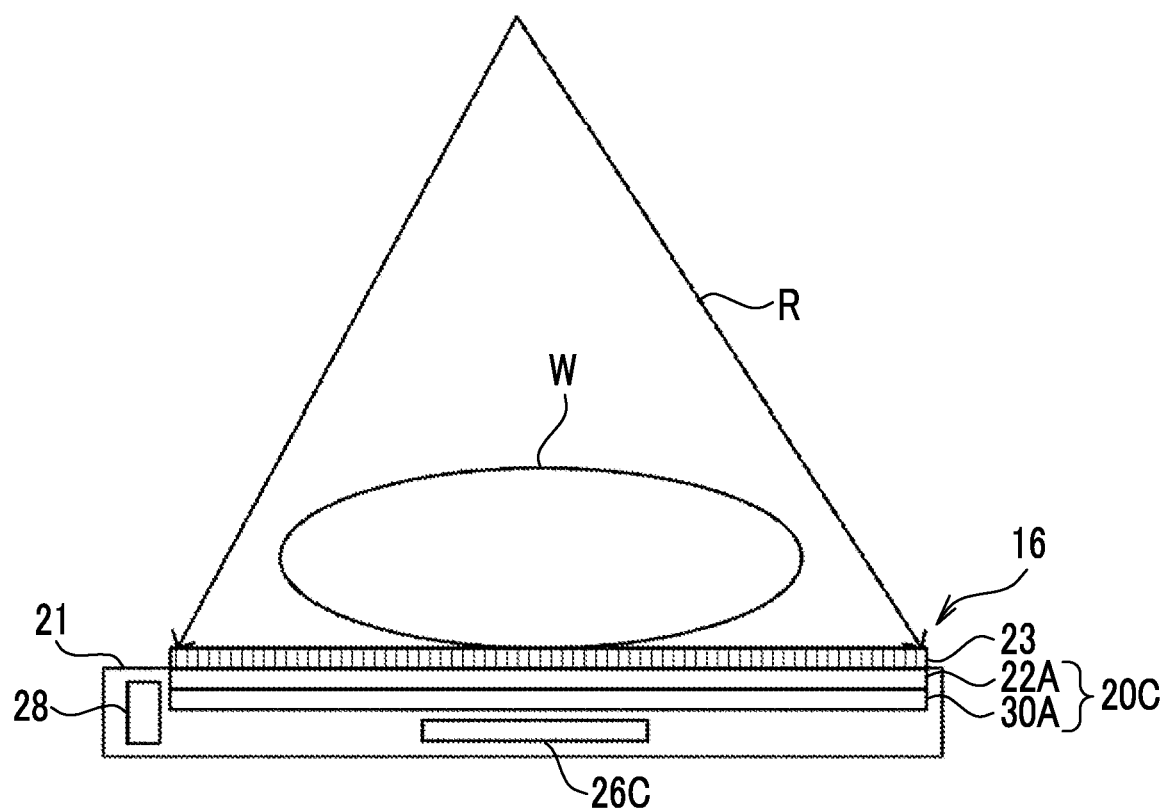
FIG. 12 is a side cross-sectional view showing another example of the configuration of a radiography apparatus according to each exemplary embodiment.

In each exemplary embodiment described above, an aspect in which the radiography apparatus 16 comprises two radiation detector 20 (20A, 20B), and the first radiographic image data 91 of the first radiographic image and the second radiographic image data 92 of the second radiographic image are obtained by one irradiation of the radiation R is described, but the present invention is not limited to the aspect. For example, as shown in FIG. 12, the radiography apparatus 16 may comprise one radiation detector 20C and a control substrate 26C corresponding to the radiation detector 20C. In the case of the form shown in FIG. 12, the radiation emitting apparatus 12 emits the radiation R by changing the tube voltage, and the radiation detector 20C performs imaging twice. Due to the different tube voltages, the radiation detector 20C is irradiated with the radiation R having different energies. In this case, the first radiographic image is a radiographic image generated by the radiation detector 20C in a case where the radiation R of the first energy is irradiated, and the second radiographic image is a radiographic image generated by the radiation detector 20C in a case where the radiation R of the second energy different from the first energy is irradiated.

It should be noted that as in the radiography apparatus 16 according to the present exemplary embodiment, by providing two radiation detector 20, the bone density of the subject W can be derived by one irradiation of the radiation R, so that the amount of irradiation of the radiation R to the subject W can be reduced to derive the bone density of the subject W, which is preferable from the viewpoint of exposure.

In the first exemplary embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B. In addition, for example, a conversion layer that absorbs radiation and converts the radiation into charge in the direct-conversion-type radiation detector is made of amorphous selenium (a-Se) and crystalline cadmium telluride (crystalline CdTe).

In the first exemplary embodiment, the case in which the ISS radiation detectors in which the radiation R is incident from the TFT substrates 30A and 30B are applied to the first radiation detector 20A and the second radiation detector 20B, respectively, has been described. However, the invention is not limited thereto. For example, a penetration side sampling (PSS) radiation detector in which the radiation R is incident from the scintillator 22A or 22B may be applied to at least one of the first radiation detector 20A or the second radiation detector 20B.

In addition, various kinds of processors other than the CPU may execute various kinds of processing executed by the CPU executing software (program) in each exemplary embodiment described above. Examples of the processors in this case include a programmable logic device (PLD) whose circuit configuration can be changed after the manufacture of a field-programmable gate array (FPGA) or the like, and a dedicated electric circuit which is a processor having a circuit configuration specifically designed for executing specific processing such as an application specific integrated circuit (ASIC) or the like. In addition, the various kinds of processing described above may be executed by one of the various kinds of processors or by a combination of two or more processors of the same type or different types (for example, a plurality of FPGAs and combinations of CPUs and FPGAs). Further, the hardware structure of the various kinds of processors is, more specifically, an electric circuit in which circuit elements such as semiconductor elements are combined.

In each exemplary embodiment described above, an aspect in which the image processing program 73 is stored (installed) in the storage unit 72 in advance is described, but the present invention is not limited to this. The image processing program 73 may be recorded on a recording medium, such as a compact disk read only memory (CD-ROM), a digital versatile disk read only memory (DVD-ROM), or a universal serial bus (USB) memory, and then provided. In addition, the image processing program 73 may be downloaded from an external apparatus through the network.

The disclosure of Japanese Patent Application No. 2018-102652 filed on May 29, 2018 is incorporated into the present specification by reference.

All of the documents, the patent applications, and the technical standards described in the present specification are incorporated herein by reference to the same degree as in a case where each of the documents, the patent applications, and the technical standards is specifically and individually written to be incorporated by reference.

What is claimed is:

1. An image processing apparatus comprising:
    a memory; and
    a processor coupled to the memory, the processor configured to:
  acquire a radiographic image captured by a radiography apparatus according to an imaging order including a plurality of examination purposes from the radiography apparatus, the plurality of examination purposes including observation of a subject and measurement of at least one of a bone density or a bone mineral content of the subject;
    perform predetermined processing for each corresponding examination purpose on the acquired radiographic image, the predetermined processing including first processing of generating a radiographic image for the observation, and second processing of deriving at least one of the bone density or the bone mineral content;
    output each processing result of the processing performed for each examination purpose to devices outside the image processing apparatus; and
    perform one of a first control for outputting the processing result at timings that are considered to be the same, or a second control for sequentially outputting the processing result in response to an end of the processing, according to settings set by a user, wherein, in a case in which the first processing ends before the second processing in the second control, the processor outputs the radiographic image for the observation generated by the first processing, wherein, in a case in which the second processing ends after the output of the radiographic image for the observation, the processor outputs an image in which information representing at least one of the bone density or the bone mineral content delivered by the second processing is added to the radiographic image for the observation generated by the first processing, wherein, in a case in which the second processing ends before the first processing in the second control, output information representing at least one of the bone density or the bone mineral content delivered by the second processing, and wherein, in a case in which the first processing ends after output of information representing at least one of the bone density or the bone mineral content, re-output an image in which information representing at least one of the bone density or the bone mineral content delivered by the second processing is added to the radiographic image for the observation generated by the first processing.

2. The image processing apparatus according to claim 1, wherein the timings that are considered to be the same are timings at which an output interval between a plurality of the processing results is equal to or less than a predetermined threshold value.

3. The image processing apparatus according to claim 1, wherein the processor is configured to perform a plurality of examination processing for each examination purpose.

4. The image processing apparatus according to claim 1, wherein the processor is configured to:
acquire a first radiographic image captured by irradiating the same subject with radiation of a first energy and a second radiographic image captured by irradiating the same subject with radiation of a second energy different from the first energy from the radiography apparatus,
perform the first processing by using the first radiographic image, and
perform the second processing by using the first radiographic image and the second radiographic image.

5. The image processing apparatus according to claim 4, wherein:
a first radiation detector and a second radiation detector in which a plurality of pixels are disposed, each of which includes a conversion element in which a generated electric charge increases with an increase in a dose of irradiated radiation, are disposed along a direction of irradiation with the radiation, in the radiography apparatus,
the first radiographic image is a radiographic image generated by the first radiation detector, and
the second radiographic image is a radiographic image generated by the second radiation detector.

6. The image processing apparatus according to claim 4, wherein:
a radiation detector in which a plurality of pixels are disposed, each of which includes a conversion element in which a generated electric charge increases with an increase in a dose of irradiated radiation, is disposed in the radiography apparatus,
the first radiographic image is a radiographic image generated by the radiation detector due to irradiation with the radiation of the first energy, and
the second radiographic image is a radiographic image generated by the radiation detector due to irradiation with the radiation of the second energy different from the first energy.

7. The image processing apparatus according to claim 1, wherein the processor is configured to perform processing of further deriving information on a comparison result between at least one of the bone density or the bone mineral content in the past of the same subject and at least one of the derived bone density or bone mineral content.

8. A radiography system comprising:
a radiography apparatus that captures a radiographic image according to an imaging order including a plurality of examination purposes; and
the image processing apparatus according to claim 1 that acquires the radiographic image from the radiography apparatus.

9. The image processing apparatus according to claim 1, wherein the processor is configured to:
in a case in which the first processing and the second processing ends in the first control, output an image in which information representing at least one of the bone density or the bone mineral content delivered by the second processing is added to the radiographic image for the observation generated by the first processing.

10. An image processing apparatus comprising:
a memory; and
a processor coupled to the memory, the processor configured to:
acquire a radiographic image captured by a radiography apparatus according to an imaging order including a plurality of examination purposes from the radiography apparatus, the plurality of examination purposes including observation of a subject and measurement of at least one of a bone density or a bone mineral content of the subject;
perform predetermined processing for each corresponding examination purpose on the acquired radiographic image, the predetermined processing including first processing of generating a radiographic image for the observation, and second processing of deriving at least one of the bone density or the bone mineral content;
output each processing result of the processing performed for each examination purpose to devices outside the image processing apparatus; and
perform one of a first control for outputting the processing result on a condition that two or more processing have been ended, or a second control for sequentially outputting the processing result to the devices outside on a condition that each processing has been ended, according to settings set by a user,
wherein, in a case in which the first processing ends before the second processing in the second control, the processor outputs the radiographic image for the observation generated by the first processing,
wherein, in a case in which the second processing ends after the output of the radiographic image for the observation, the processor outputs an image in which information representing at least one of the bone density or the bone mineral content delivered by the second processing is added to the radiographic image for the observation generated by the first processing,
wherein, in a case in which the second processing ends before the first processing in the second control, output information representing at least one of the bone density or the bone mineral content delivered by the second processing, and wherein, in a case in which the first processing ends after output of information representing at least one of the bone density or the bone mineral content, re-output an image in which information representing at least one of the bone density or the bone mineral content delivered by the second processing is added to the radiographic image for the observation generated by the first processing.

11. An image processing method comprising:
acquiring a radiographic image captured by a radiography apparatus according to an imaging order including a plurality of examination purposes from the radiography apparatus;
performing predetermined processing for each corresponding examination purpose on the acquired radiographic image, the predetermined processing including first processing of generating a radiographic image for the observation, and second processing of deriving at least one of the bone density or the bone mineral content;
outputting each processing result of the processing performed for each examination purpose to devices outside the image processing apparatus; and
performing one of a first control for outputting the processing result at timings that are considered to be the same or a second control for sequentially outputting the processing result in response to an end of the processing, according to settings set by a user,
wherein, in a case in which the first processing ends before the second processing in the second control, the radiographic image for the observation generated by the first processing is output,
wherein, in a case in which the second processing ends after the output of the radiographic image for the observation, an image is output in which information representing at least one of the bone density or the bone mineral content delivered by the second processing is added to the radiographic image for the observation generated by the first processing,
wherein, in a case in which the second processing ends before the first processing in the second control, output information representing at least one of the bone density or the bone mineral content delivered by the second processing, and
wherein, in a case in which the first processing ends after output of information representing at least one of the bone density or the bone mineral content, re-output an image in which information representing at least one of the bone density or the bone mineral content delivered by the second processing is added to the radiographic image for the observation generated by the first processing.

12. An image processing method comprising:
acquiring a radiographic image captured by a radiography apparatus according to an imaging order including a plurality of examination purposes from the radiography apparatus;
performing predetermined processing for each corresponding examination purpose on the acquired radiographic image, the predetermined processing including first processing of generating a radiographic image for the observation, and second processing of deriving at least one of the bone density or the bone mineral content;
outputting each processing result of the processing performed for each examination purpose to devices outside the image processing apparatus; and
performing one of a first control for outputting the processing result on a condition that two or more processing have been ended or a second control for sequentially outputting the processing result to the devices outside on a condition that each processing has been ended, according to settings set by a user,
wherein, in a case in which the first processing ends before the second processing in the second control, the radiographic image for the observation generated by the first processing is output,
wherein, in a case in which the second processing ends after the output of the radiographic image for the observation, an image is output in which information representing at least one of the bone density or the bone mineral content delivered by the second processing is added to the radiographic image for the observation generated by the first processing,
wherein, in a case in which the second processing ends before the first processing in the second control, output information representing at least one of the bone density or the bone mineral content delivered by the second processing, and
wherein, in a case in which the first processing ends after output of information representing at least one of the bone density or the bone mineral content, re-output an image in which information representing at least one of the bone density or the bone mineral content delivered by the second processing is added to the radiographic image for the observation generated by the first processing.

13. A non-transitory computer-readable medium storing an image processing program executable by a computer to perform a process, the process comprising:
acquiring a radiographic image captured by the radiography apparatus according to an imaging order including a plurality of examination purposes from a radiography apparatus;
performing predetermined processing for each corresponding examination purpose on the acquired radiographic image acquired, the predetermined processing including first processing of generating a radiographic image for the observation, and second processing of deriving at least one of the bone density or the bone mineral content;
outputting each processing result of the processing performed for each examination purpose to devices outside the image processing apparatus; and
performing one of a first control for outputting the processing result at timings that are considered to be the same or a second control for sequentially outputting the processing result in response to an end of the processing, according to settings set by a user,
wherein, in a case in which the first processing ends before the second processing in the second control, the radiographic image for the observation generated by the first processing is output,
wherein, in a case in which the second processing ends after the output of the radiographic image for the observation, an image is output in which information representing at least one of the bone density or the bone mineral content delivered by the second processing is added to the radiographic image for the observation generated by the first processing,
wherein, in a case in which the second processing ends before the first processing in the second control, output information representing at least one of the bone density or the bone mineral content delivered by the second processing, and wherein, in a case in which the first processing ends after output of information representing at least one of the bone density or the bone mineral content, re-output an image in which information representing at least one of the bone density or the bone mineral content delivered by the second processing is added to the radiographic image for the observation generated by the first processing.

14. A non-transitory computer-readable medium storing an image processing program executable by a computer to perform a process, the process comprising:

acquiring a radiographic image captured by a radiography apparatus according to an imaging order including a plurality of examination purposes from the radiography apparatus;

performing predetermined processing for each corresponding examination purpose on the acquired radiographic image, the predetermined processing including first processing of generating a radiographic image for the observation, and second processing of deriving at least one of the bone density or the bone mineral content;

outputting each processing result of the processing performed for each examination purpose to devices outside the image processing apparatus; and performing one of a first control for outputting the processing result on a condition that two or more processing have been ended or a second control for sequentially outputting the processing result to the devices outside on a condition that each processing has been ended, according to settings set by a user, wherein, in a case in which the first processing ends before the second processing in the second control, the radiographic image for the observation generated by the first processing is output, wherein, in a case in which the second processing ends after the output of the radiographic image for the observation, an image is output in which information representing at least one of the bone density or the bone mineral content delivered by the second processing is added to the radiographic image for the observation generated by the first processing, wherein, in a case in which the second processing ends before the first processing in the second control, output information representing at least one of the bone density or the bone mineral content delivered by the second processing, and wherein, in a case in which the first processing ends after output of information representing at least one of the bone density or the bone mineral content, re-output an image in which information representing at least one of the bone density or the bone mineral content delivered by the second processing is added to the radiographic image for the observation generated by the first processing.

* * * * *